United States Patent
Itoi

(10) Patent No.: US 10,741,774 B2
(45) Date of Patent: Aug. 11, 2020

(54) HETEROCYCLIC COMPOUND AND ORGANIC ELECTROLUMINESCENCE DEVICE INCLUDING THE SAME

(71) Applicant: Samsung Display Co., Ltd., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 269 days.

(21) Appl. No.: 15/839,740

(22) Filed: Dec. 12, 2017

(65) Prior Publication Data

US 2019/0013480 A1 Jan. 10, 2019

(30) Foreign Application Priority Data

Jul. 4, 2017 (KR) ........................ 10-2017-0085060

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/82* (2013.01); *C07D 239/24* (2013.01); *C07D 251/12* (2013.01); *C09K 11/06* (2013.01)

(58) Field of Classification Search
None
See application file for complete search history.

(56) References Cited

U.S. PATENT DOCUMENTS 8,324,403 B2 12/2012 Yabe et al.
2008/0145699 A1* 6/2008 Yabe ............... C07D 209/86
428/690

(Continued)

FOREIGN PATENT DOCUMENTS

JP 4416074 2/2010
JP 5050344 10/2012

(Continued)

*Primary Examiner* — Gregory D Clark
(74) *Attorney, Agent, or Firm* — Lewis Roca Rothgerber Christie LLP

(57) ABSTRACT

A heterocyclic compound represented by Formula 1 and an organic electroluminescence device including the same in an emission layer.

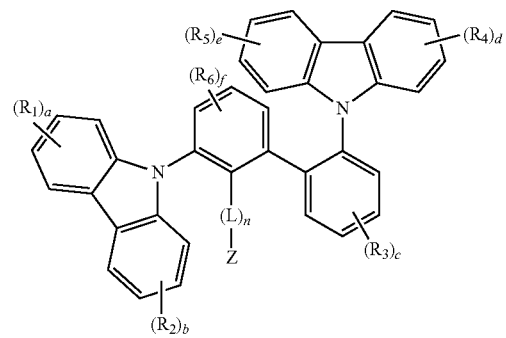

Formula 1

In Formula 1, Z is represented by Formula 2-1 or 2-2.
(Continued)

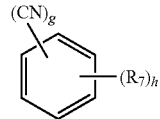

Formula 2-1

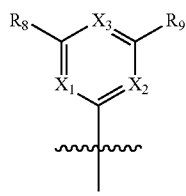

Formula 2-2

In Formula 2-2, $X_1$ to $X_3$ are each independently $CR_{10}$ or N, and at least one of $X_1$ to $X_3$ is N.

20 Claims, 1 Drawing Sheet

(51) Int. Cl.
    *C09K 11/06*     (2006.01)
    *C07D 251/12*     (2006.01)
    *C07D 239/24*     (2006.01)
    *C07D 209/82*     (2006.01)

(56) References Cited

U.S. PATENT DOCUMENTS

| | | |
|---|---|---|
| 2016/0013423 A1 | 1/2016 | Huh et al. |
| 2017/0062752 A1 | 3/2017 | Ihn et al. |
| 2017/0098780 A1 | 4/2017 | Kim et al. |
| 2017/0358755 A1* | 12/2017 | Jung .................... C07D 209/86 |

FOREIGN PATENT DOCUMENTS

| | | |
|---|---|---|
| JP | 2016-17078 A | 2/2016 |
| KR | 10-2016-0006629 | 1/2016 |
| KR | 10-2017-0026075 | 3/2017 |
| KR | 10-2017-0040697 | 4/2017 |
| WO | WO 2016/159479 A1 | 10/2016 |
| WO | WO 2016/181846 A1 | 11/2016 |

* cited by examiner

HETEROCYCLIC COMPOUND AND ORGANIC ELECTROLUMINESCENCE DEVICE INCLUDING THE SAME

CROSS-REFERENCE TO RELATED APPLICATION

This application claims priority to and the benefit of Korean Patent Application No. 10-2017-0085060, filed in the Korean Intellectual Property Office on Jul. 4, 2017, the entire content of which is incorporated herein by reference.

BACKGROUND

1. Field

The present disclosure herein relates to a heterocyclic compound and an organic electroluminescence device including the same.

2. Description of the Related Art

The development of an organic electroluminescence display as an image display device is being actively conducted. The organic electroluminescence display is different from a liquid crystal display and is a self-luminescent display, accomplishing the display (e.g., of an image) via the recombination of holes and electrons injected from a first electrode and a second electrode in an emission layer and via light emission from a luminescent material including an organic compound in the emission layer.

As an organic electroluminescence device, a related art organic device includes, for example, a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer into the emission layer. Meanwhile, electrons are injected from the second electrode, and the injected electrons move via the electron transport layer into the emission layer. The holes and electrons injected into the emission layer recombine to produce excitons in the emission layer. The organic electroluminescence device emits light generated by the transition of the excitons to a ground state. The configuration of the organic electroluminescence device is not limited thereto, but various suitable modifications may be possible.

SUMMARY

Aspects according to one or more embodiments of the present disclosure are directed toward a heterocyclic compound and an organic electroluminescence device including the same. More particularly, aspects according to one or more embodiments of the present disclosure are directed toward a heterocyclic compound for a thermally activated delayed fluorescence material and an organic electroluminescence device including the same.

According to an embodiment of the present disclosure, a heterocyclic compound is represented by the following Formula 1 and has an absolute value of a difference between a singlet energy level and a triplet energy level of about 0.2 eV or less:

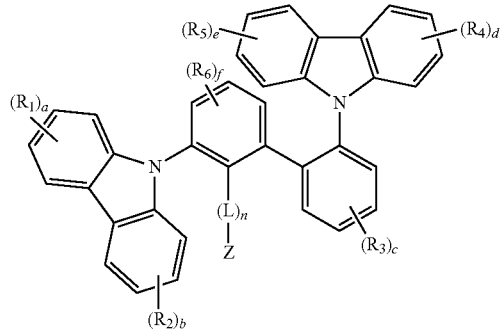

Formula 1

In Formula 1, $R_1$ to $R_6$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring; L is a substituted or unsubstituted arylene group having 6 to 30 carbon atoms for forming a ring, or a substituted or unsubstituted heteroarylene group having 2 to 30 carbon atoms for forming a ring; a to e are each independently an integer of 0 to 4, f is an integer of 0 to 3, n is 0 or 1; and Z is represented by the following Formula 2-1 or Formula 2-2:

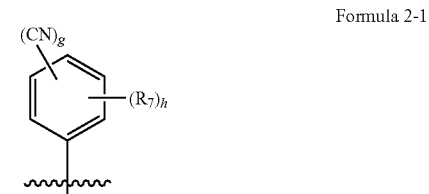

Formula 2-1

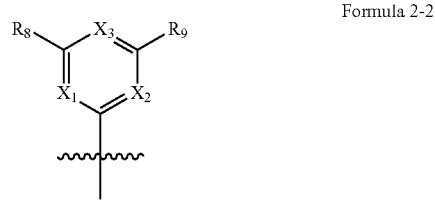

Formula 2-2

In Formula 2-1, g is 1 or 2. When g is 1, h is an integer of 0 to 4, and when g is 2, h is an integer of 0 to 3. $R_7$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In Formula 2-2, $X_1$ to $X_3$ are each independently $CR_{10}$ or N, at least one of $X_1$ to $X_3$ is N; and $R_8$ to $R_{10}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In an embodiment, Z may be represented by one of the following Formulae 3-1 to 3-9:

Formula 3-1
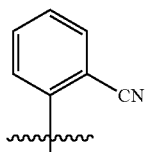

Formula 3-2
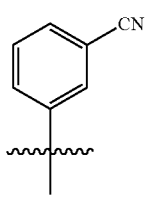

Formula 3-3
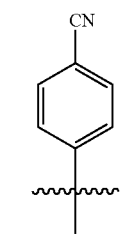

Formula 3-4
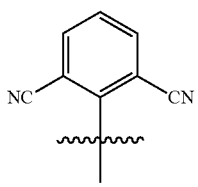

Formula 3-5
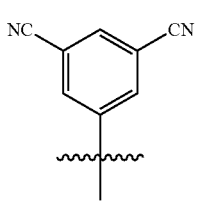

Formula 3-6
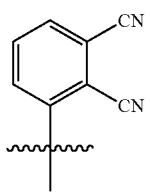

Formula 3-7
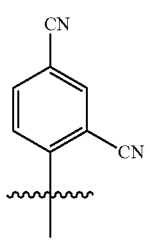

Formula 3-8
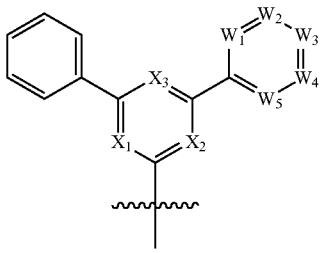

Formula 3-9

In an embodiment, Z may be represented by the following Formula 2-2-1:

Formula 2-2-1

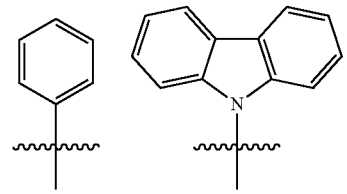

In Formula 2-2-1, $W_1$ to $W_5$ are each independently CH or N, and $X_1$ to $X_3$ are the same as described above. The total number of N in $W_1$ to $W_5$ may be 0 or 1.

In an embodiment, L may be a substituted or unsubstituted phenylene group.

In an embodiment, at least one of $R_1$, $R_2$, $R_4$, and $R_5$ may be a substituted or unsubstituted phenyl group, or a substituted or unsubstituted carbazole group.

In an embodiment, at least one of $R_1$, $R_2$, $R_4$, and $R_5$ may be represented by one of the following structures:

In an embodiment, a+b+d+e may be 0, 1 or 2.

In an embodiment of the present disclosure, an organic electroluminescence device includes a first electrode, a hole transport region on the first electrode, an emission layer on the hole transport region, an electron transport region on the emission layer, and a second electrode on the electron transport region, wherein the emission layer includes the heterocyclic compound according to an embodiment of the present disclosure.

In an embodiment, the heterocyclic compound according to an embodiment of the present disclosure may be a material to emit blue light having a wavelength of less than about 470 nm.

In an embodiment, the heterocyclic compound according to an embodiment of the present disclosure may be a material to emit thermally activated delayed fluorescence.

BRIEF DESCRIPTION OF THE FIGURES

The accompanying drawings are included to provide a further understanding of the present disclosure, and are incorporated in and constitute a part of this disclosure. The drawings illustrate exemplary embodiments of the present disclosure and, together with the description, serve to explain principles of the present disclosure. In the drawings.

DETAILED DESCRIPTION

Figure 1:
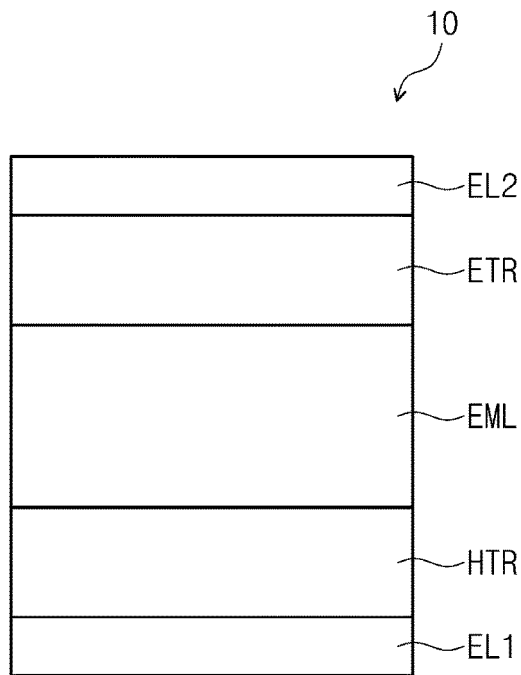
FIG. 1 is a cross-sectional view schematically illustrating an organic electroluminescence device according to an embodiment of the present disclosure.

The features and enhancements of the present disclosure will be easily understood from preferred exemplary embodiments with reference to the accompanying drawings. The present disclosure may, however, be embodied in different forms and should not be construed as limited to the embodiments set forth herein. Rather, these embodiments are provided so that the disclosed contents are thorough and complete, and fully convey the spirit of the present disclosure to a person skilled in the art.

Like reference numerals refer to like elements for explaining each drawing. In the drawings, the sizes of elements may be enlarged for clarity of the present disclosure. It will be understood that, although the terms first, second, etc., may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc., is referred to as being "on" or "under" another part, it can be directly on or directly under the other part, or intervening layers, films, regions, plates, etc., may also be present.

In the present disclosure,  indicates a part to be connected (i.e., a bonding site).

In the present disclosure, the term "substituted" may refer to a compound in which at least one hydrogen atom is substituted with at least one substituent selected from a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle. In addition, each of the substituent illustrated above may be substituted or unsubstituted. For example, a biphenyl group may be interpreted as an aryl group, or a phenyl group substituted with a phenyl group.

In the present disclosure, the term "a halogen atom" may refer to a fluorine atom, a chlorine atom, a bromine atom, and/or an iodine atom.

In the present disclosure, the term "alkyl group" may refer to a group having a linear or branched chain, or a cycle shape. The carbon number of the alkyl group may be 1 to 30, 1 to 20, 1 to 10, or 1 to 6. Non-limiting examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the term "aryl group" may refer to a functional group or a substituent (e.g., an optional functional group or substituent) derived from an aromatic cyclic hydrocarbon. The aryl group may be monocyclic aryl or polycyclic aryl. The carbon number of the aryl group for forming a ring may be 6 to 30, 6 to 20, or 6 to 15. Non-limiting examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc.

In the present disclosure, the term "fluorenyl group" may include an unsubstituted or substituted fluorenyl group, and two substituents may be combined with each other to form a spiro structure. Examples of the substituted fluorenyl group are as follows. However, an embodiment of the present disclosure is not limited thereto.

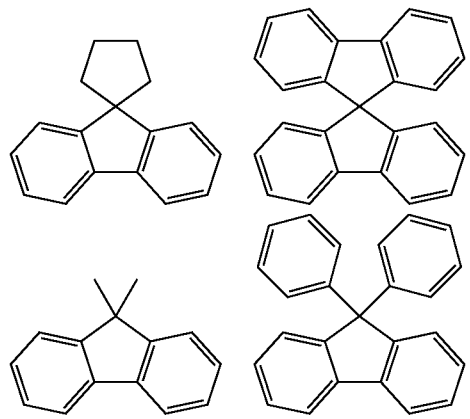

In the present disclosure, the term "heteroaryl group" may refer to a heteroaryl group including at least one of O, N, P, Si or S as a ring forming heteroatom. When the heteroaryl group includes two heteroatoms, the two heteroatoms may be the same or different from each other. The carbon number of the heteroaryl group for forming a ring may be 2 to 30, or 2 to 20. The heteroaryl group may be monocyclic heteroaryl group or polycyclic heteroaryl group. The heteroaryl group may have a structure, for example, of two rings or three rings. Non-limiting examples of the heteroaryl group may include thiophenyle, furanyl, pyrrolyle, imidazolyle, thiazole, oxazolyle, oxadiazole, triazolyle, pyridyl, bipyridyl, pyrimidyl, triazinyle, triazole, acridyl, pyridazinyle, pyrazinyl, quinolinyl, quinazolinyle, quinoxalinyl, phenoxazinyl, phthalazinyl, pyrido pyrimidinyl, pyrido pyrazinyl, pyrazino pyrazinyl, isoquinolinyle, indolyle, carbazolyle, N-arylcarbazolyle, N-heteroaryl carbazolyle, N-alkyl carbazolyle, benzoxazolyle, benzoimidazolyle, benzothiazole, benzocarbazolyle, benzothiophenyle, dibenzothiophenyle, thienothiophenyle, benzofuranyl, phenanthrolinyle, thiazolyl, isooxazolyl, oxadiazolyl, thiadiazolyl, benzothiazolyl, phenothiazinyl, dibenzofuranyl, etc.

In the present disclosure, the term "silyl group" may refer to alkylsilyl group and/or arylsilyl group. Non-limiting examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc.

In the present disclosure, the term "boron group" may refer to alkyl boron group and/or aryl boron group. Non-limiting examples of the boron group may include trimethylboron, triethylboron, t-butyldimethyl boron, triphenylboron, diphenylboron, phenylboron, etc.

In the present disclosure, the alkenyl group may be linear or branched. The number of carbon atoms in the alkenyl group is not specifically limited, for example, may be 2 to 30, 2 to 20, or 2 to 10. Non-limiting examples of the alkenyl group may include vinyl, 1-butenyl, 1-pentenyl, 1,3-butadienyl aryl, styrenyl, styrylvinyl, etc.

In the present disclosure, the number of carbon atoms in the amino group is not specifically limited, for example, may be 1 to 30. The amino group may include an alkylamino group and/or an arylamino group. Non-limiting examples of the amino group may include a methylamino group, a dimethylamino group, a phenylamino group, a diphenylamino group, a naphthylamino group, a 9-methyl-anthracenylamino group, a triphenylamino group, etc.

The heterocyclic compound according to an embodiment of the present disclosure will be explained.

The heterocyclic compound according to an embodiment of the present disclosure is represented by Formula 1 below.

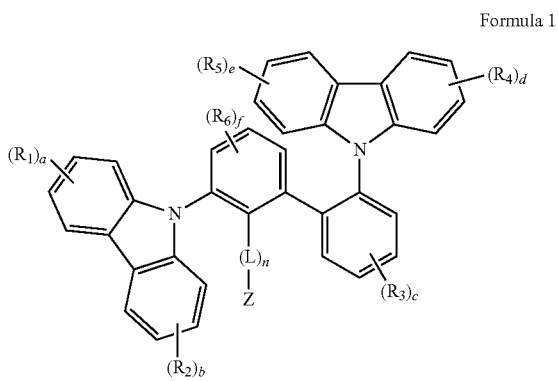

Formula 1

In Formula 1, $R_1$ to $R_6$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring; and L is a substituted or unsubstituted arylene group having 6 to 30 carbon atoms for forming a ring, or a substituted or unsubstituted heteroarylene group having 2 to 30 carbon atoms for forming a ring.

In Formula 1, a to e (i.e., a, b, c, d and e) are each independently an integer of 0 to 4, f is an integer of 0 to 3, and n is 0 or 1.

If a is 2 or more, a plurality of $R_1$s may be the same or different. If b is 2 or more, a plurality of $R_2$s may be the same or different. If c is 2 or more, a plurality of $R_3$s may be the same or different. If d is 2 or more, a plurality of $R_4$s may be the same or different. If e is 2 or more, a plurality of $R_5$s may be the same or different. If f is 2 or more, a plurality of $R_6$s may be the same or different.

In Formula 1, Z may be an electron-withdrawing group.

In Formula 1, Z is represented by the following Formula 2-1 or Formula 2-2:

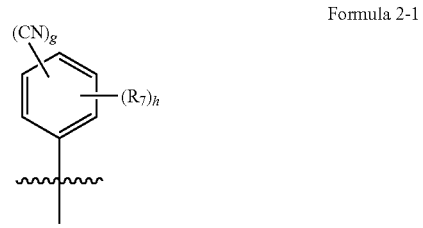

Formula 2-1

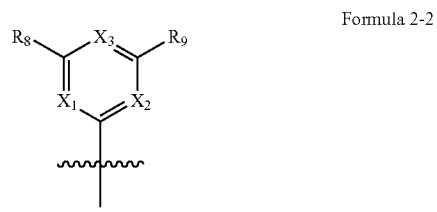

Formula 2-2

In Formula 2-1, g is 1 or 2, where if g is 1, h is an integer of 0 to 4, and if g is 2, h is an integer of 0 to 3.

If h is 2 or more, a plurality of $R_7$s may be the same or different. In one embodiment, h may be 0, but an embodiment of the present disclosure is not limited thereto.

In Formula 2-1, $R_7$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring. For example, in Formula 2-1, $R_7$ may be a hydrogen atom. However, an embodiment of the present disclosure is not limited thereto.

In Formula 2-2, $X_1$ to $X_3$ are each independently $CR_{10}$ or N, and at least one of $X_1$ to $X_3$ is N.

In Formula 2-2, $R_8$ to $R_{10}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

Z may be represented by Formula 2-1. In one embodiment, Z may be represented by one of the following Formulae 3-1 to 3-9:

Formula 3-1
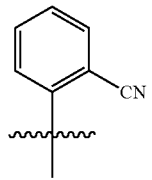

Formula 3-2
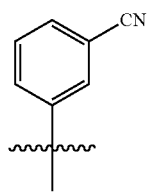

Formula 3-3
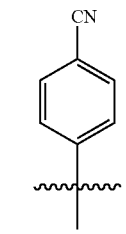

Formula 3-4
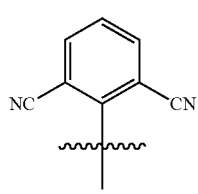

Formula 3-5
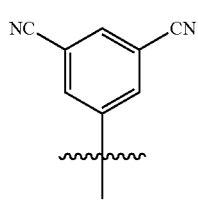

Formula 3-6
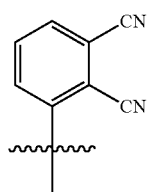

Formula 3-7
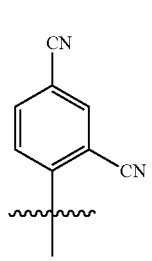

-continued

Formula 3-8
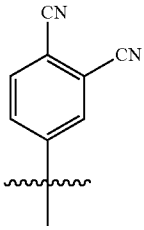

Formula 3-9
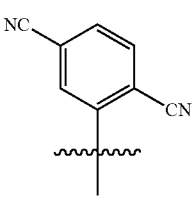

Z may be represented by Formula 2-2. In one embodiment, Z may be represented by the following Formula 2-2-1:

Formula 2-2-1
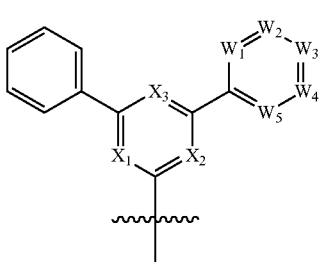

In Formula 2-2-1, $W_1$ to $W_5$ are each independently CH or N, $X_1$ to $X_3$ are the same as described above. The number (e.g., the total number) of N in $W_1$ to $W_5$ may be 0 or 1. That is, the ring including $W_1$ to $W_5$ in Formula 2-2-1 may be a substituted or unsubstituted phenyl group or a substituted or unsubstituted pyridyl group.

In Formula 2-2, $R_8$ and $R_9$ may be each independently a substituted or unsubstituted aryl group having 6 to 30 carbon atoms for forming a ring, or a substituted or unsubstituted heteroaryl group having 2 to 30 carbon atoms for forming a ring. At least one of $R_8$ and $R_9$ may be a substituted or unsubstituted aryl group having 6 to 20 carbon atoms for forming a ring. At least one of $R_8$ and $R_9$ may be a substituted or unsubstituted phenyl group. Both $R_8$ and $R_9$ may be an unsubstituted phenyl group.

In Formula 2-2, one of $R_8$ and $R_9$ may be a substituted or unsubstituted phenyl group, and the remaining one may be a substituted or unsubstituted monocyclic heteroaryl group. One of $R_8$ and $R_9$ may be a substituted or unsubstituted phenyl group, and the remaining one may be a substituted or unsubstituted pyridyl group.

In Formula 1, n may be 0. However, an embodiment of the present disclosure is not limited thereto. In one embodiment, n may be 1, and L may be a substituted or unsubstituted arylene group having 6 to 30 carbon atoms for forming a ring. For example, n may be 1, and L may be a substituted or unsubstituted phenylene group.

In Formula 1, L may be represented by one of the following structures:

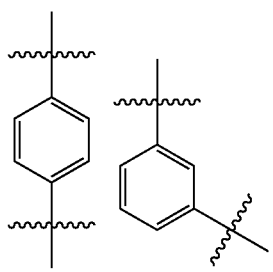

In Formula 1, a+b+d+e may be 0, 1 or 2. However, an embodiment of the present disclosure is not limited thereto.

In Formula 1, a+b+d+e may be 1 or more, and at least one of $R_1$, $R_2$, $R_4$ and $R_5$ may be a substituted or unsubstituted phenyl group, or a substituted or unsubstituted carbazolyl group. For example, at least one of $R_1$, $R_2$, $R_4$ and $R_5$ may be represented by one of the following structures:

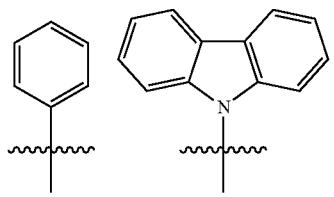

In Formula 1, c and f may each be 0. However, an embodiment of the present disclosure is not limited thereto.

The heterocyclic compound represented by Formula 1 may be represented by one of the following Formulae 1-1 to 1-3:

Formula 1-1

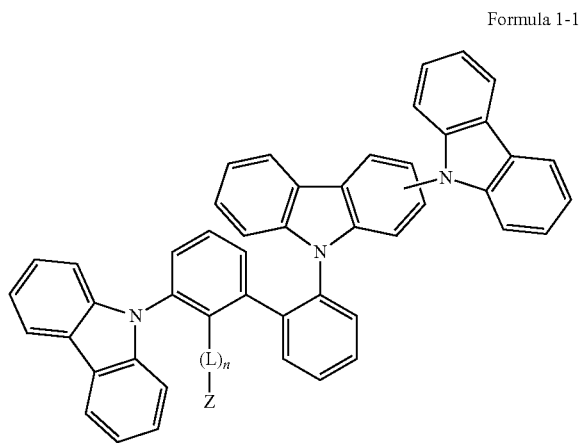

Formula 1-2

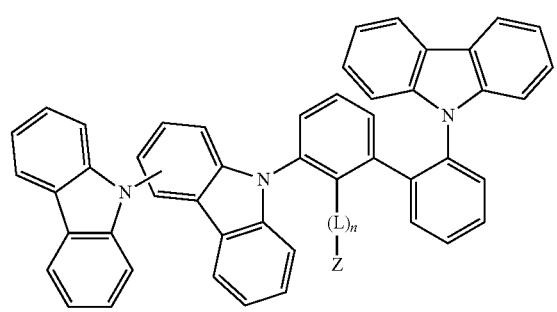

Formula 1-3

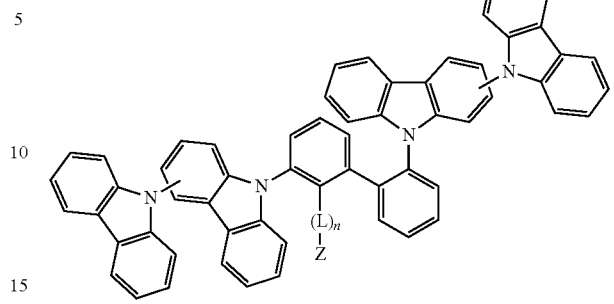

In Formulae 1-1 to 1-3, Z, L and n are substantially the same as described above.

The heterocyclic compound represented by Formula 1 may be represented by Formula 1-4 or Formula 1-5 below.

Formula 1-4

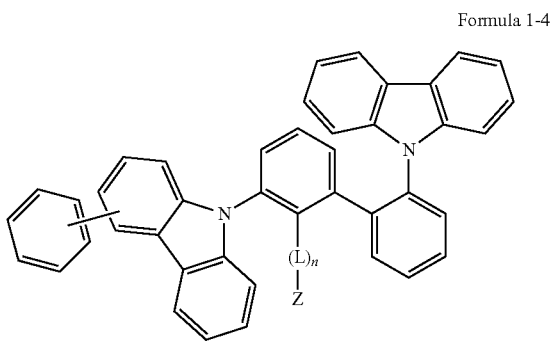

Formula 1-5

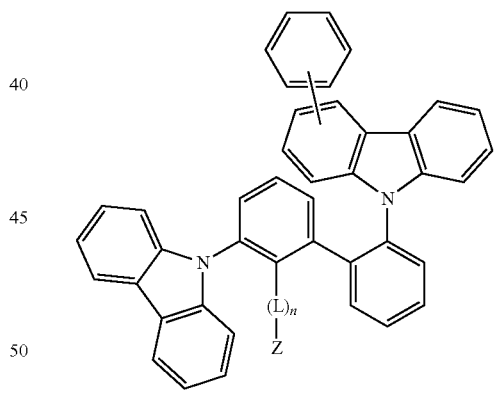

In Formulae 1-4 and 1-5, Z, L and n are substantially the same as described above.

The heterocyclic compound according to an embodiment of the present disclosure has an absolute value of a difference between a singlet energy level (S1) and a triplet energy level (T1) of about 0.2 eV or less. The heterocyclic compound according to an embodiment of the present disclosure has a small singlet-triplet energy gap, and may be utilized as an efficient material for thermally activated delayed fluorescence.

The heterocyclic compound represented by Formula 1 according to an embodiment of the present disclosure may be any one selected from the compounds represented in the following Compound Group 1. However, an embodiment of the present disclosure is not limited thereto.

Compound Group 1
T-01
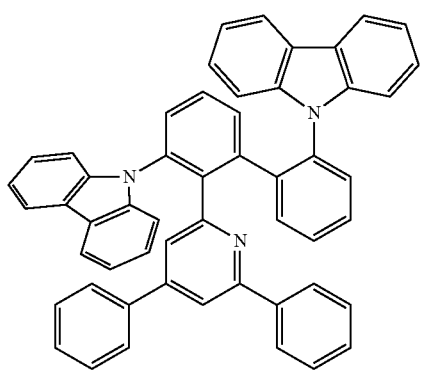
T-02
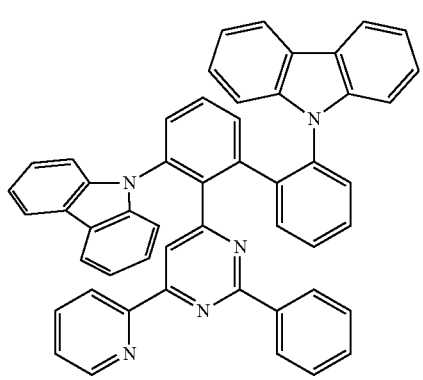
T-03
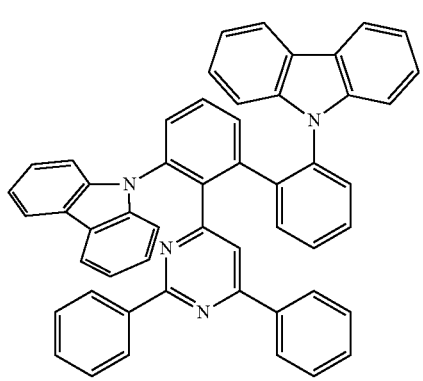
T-04
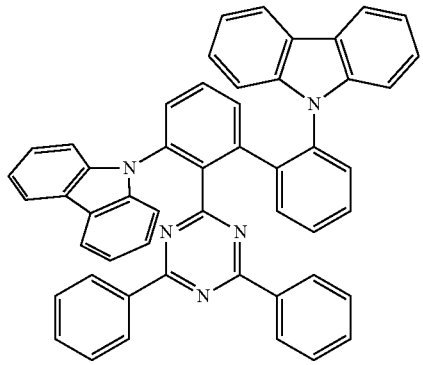
T-05
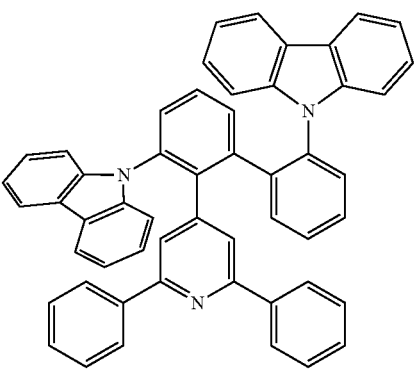
T-06
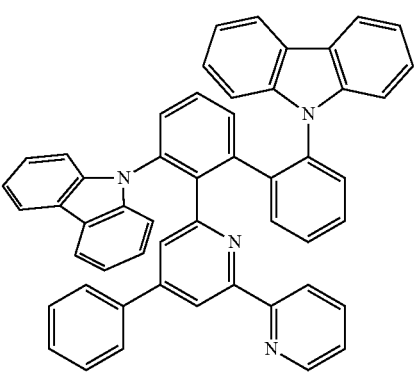
T-07
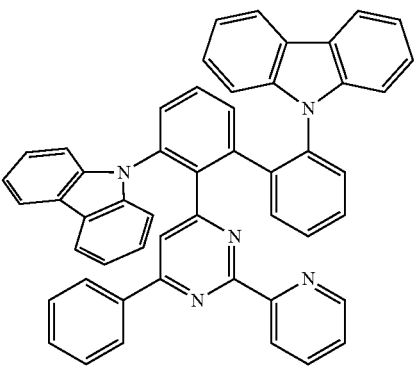
T-08
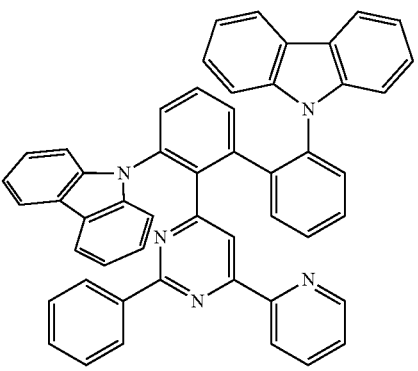

-continued
T-09
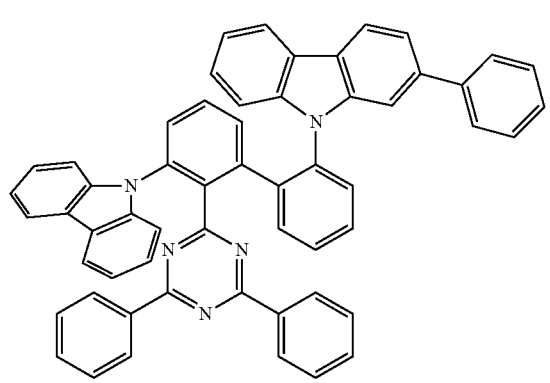
T-10
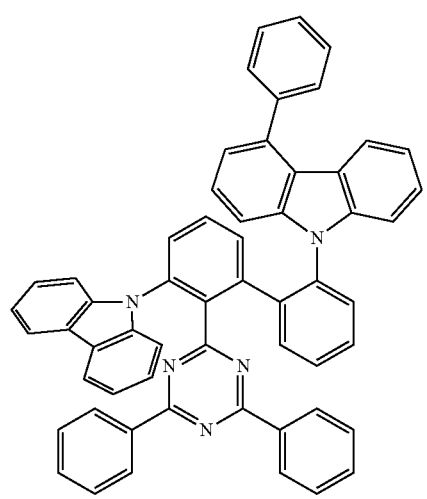
T-13
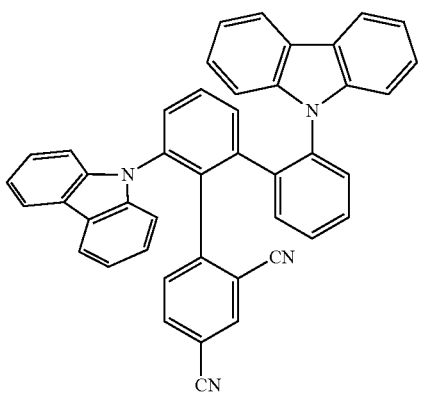
T-14
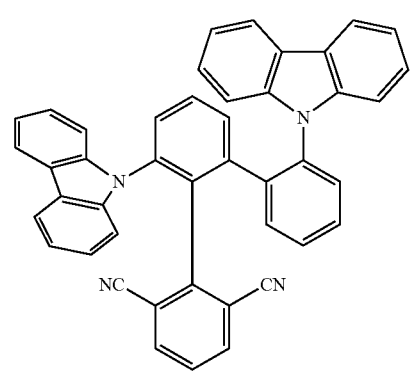
T-11
T-15
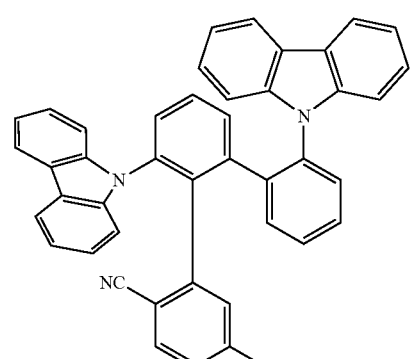
T-12
T-16
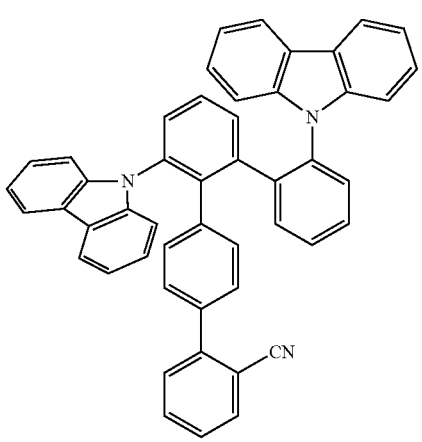

T-17
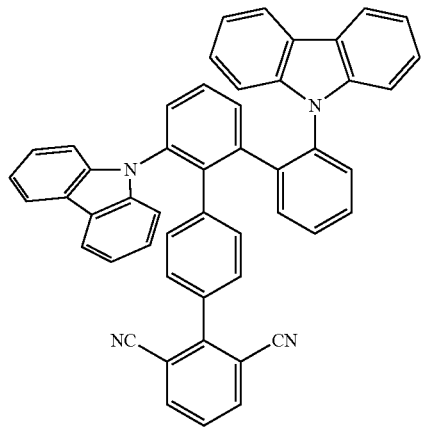
T-18
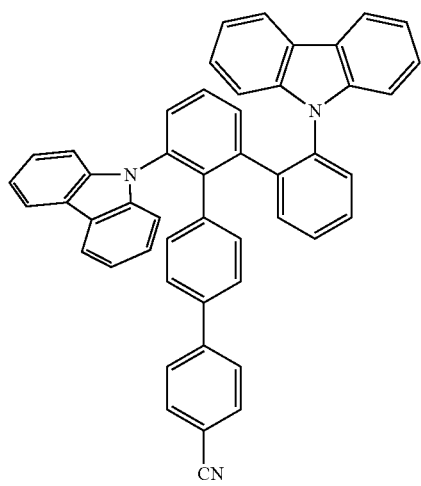
T-19
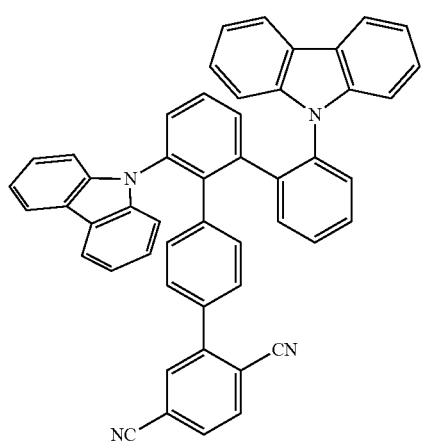
T-20
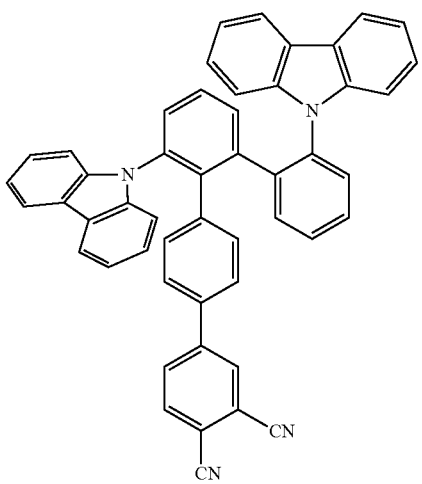
T-21
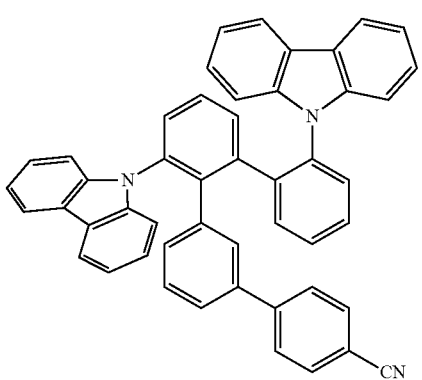
T-22
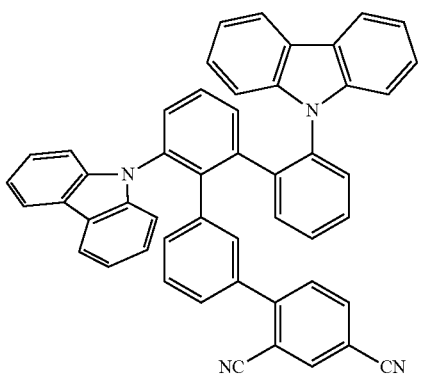
T-23
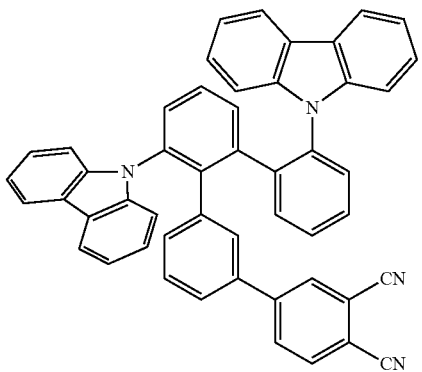

-continued
T-24
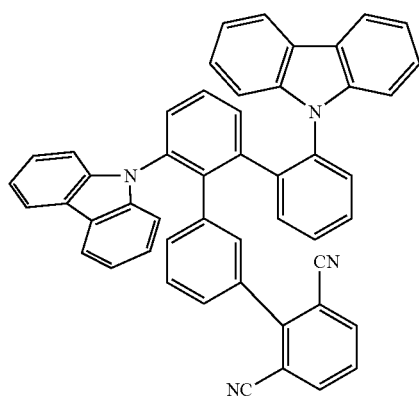
T-25
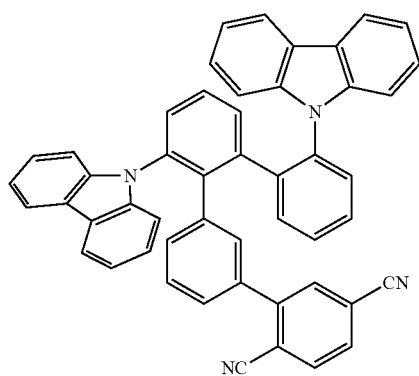
T-26
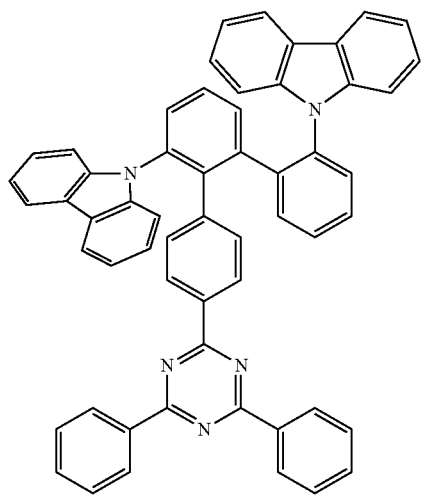
-continued
T-27
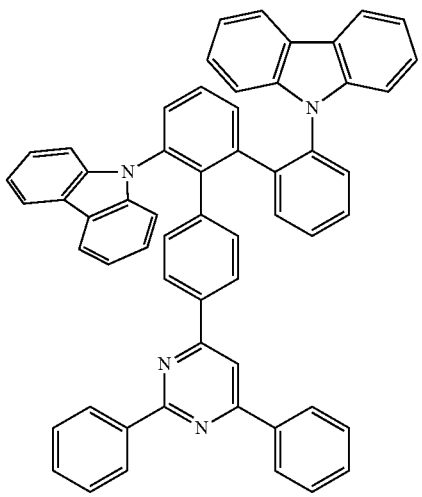
T-28
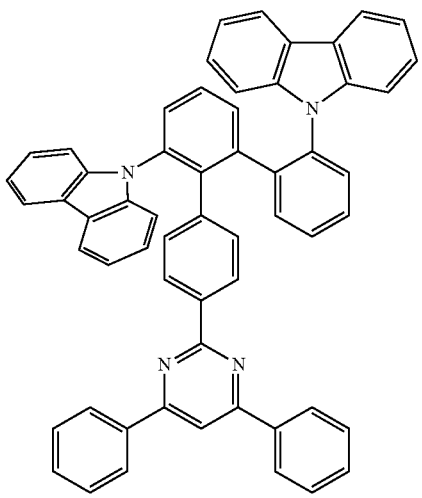
T-29
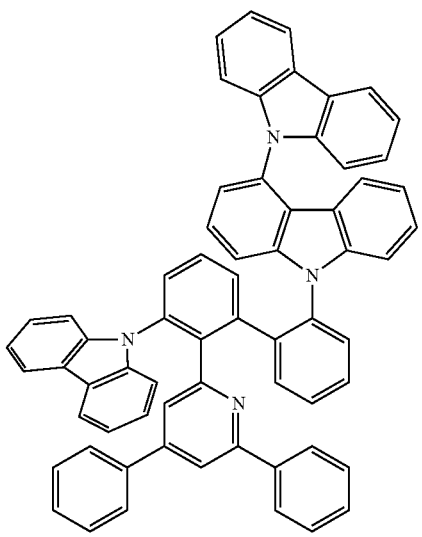

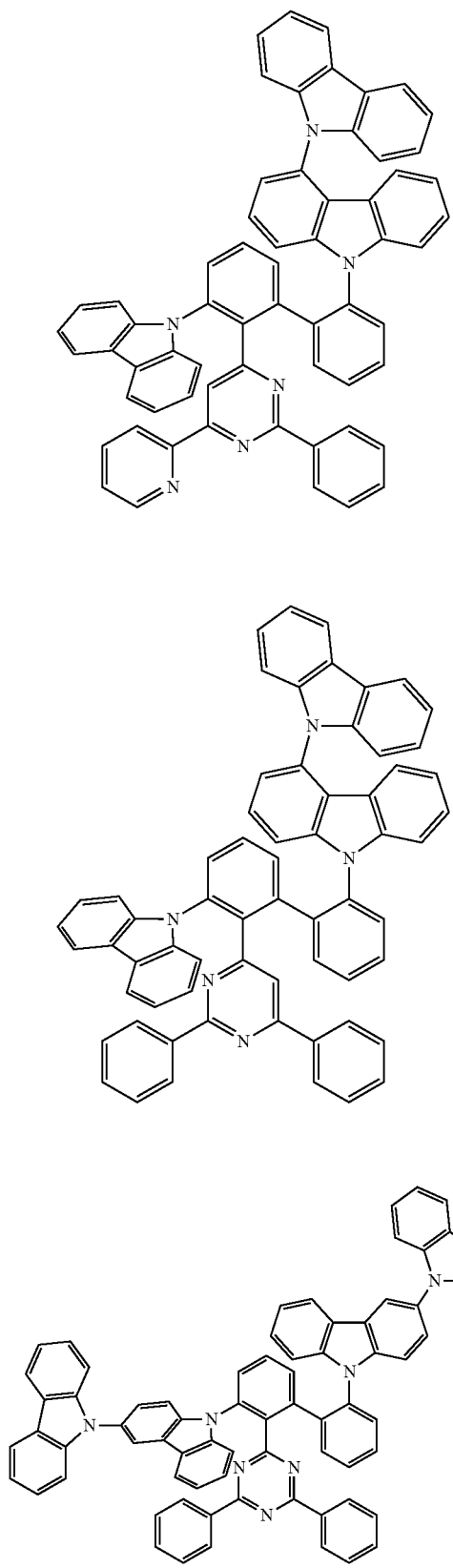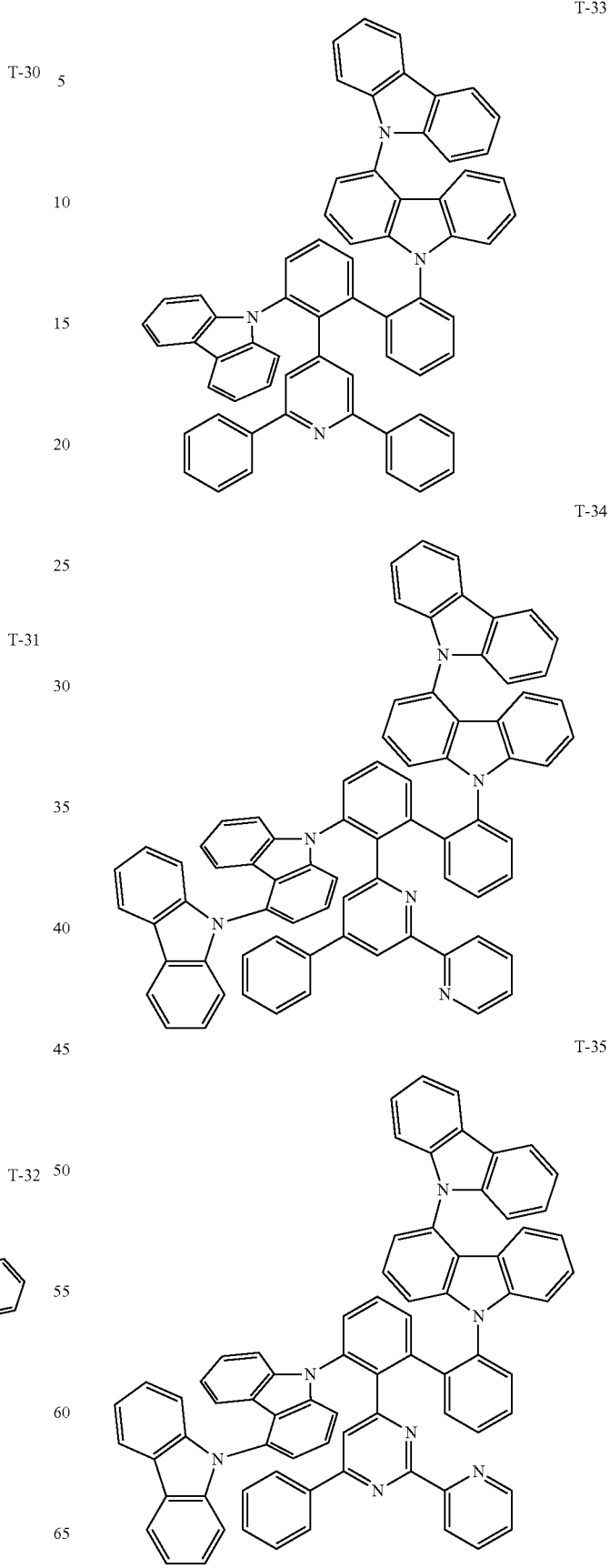

T-36
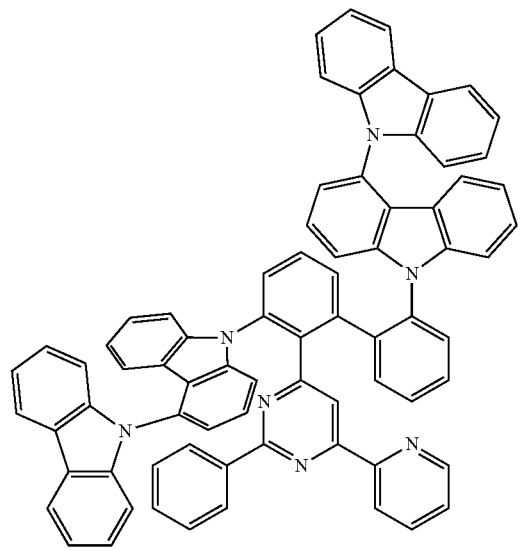
T-37
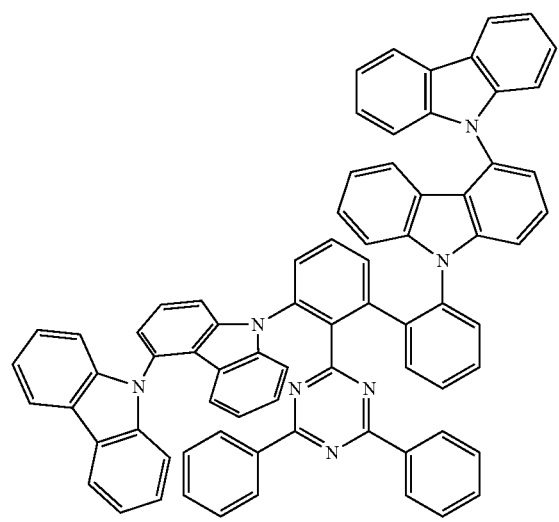
T-38
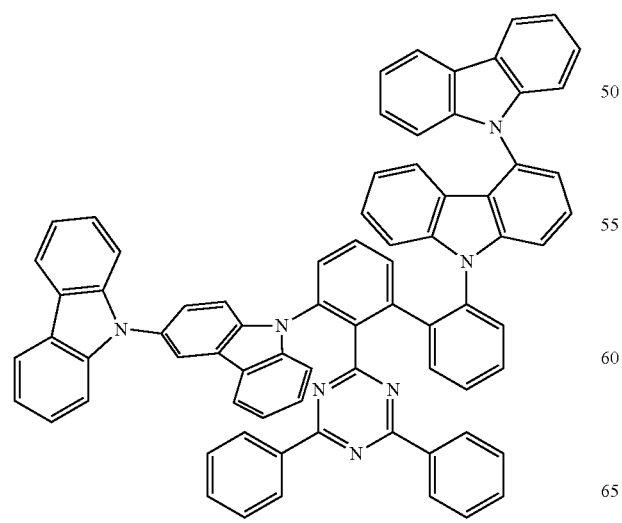
T-39
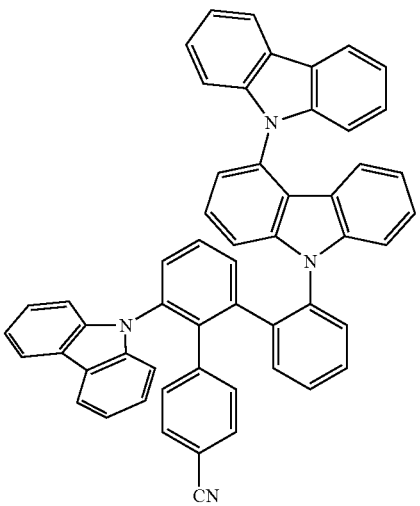
T-40
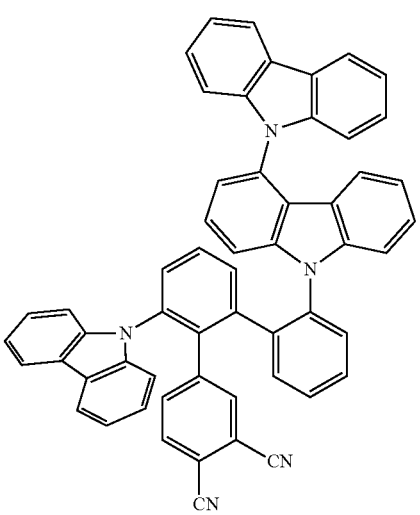
T-41
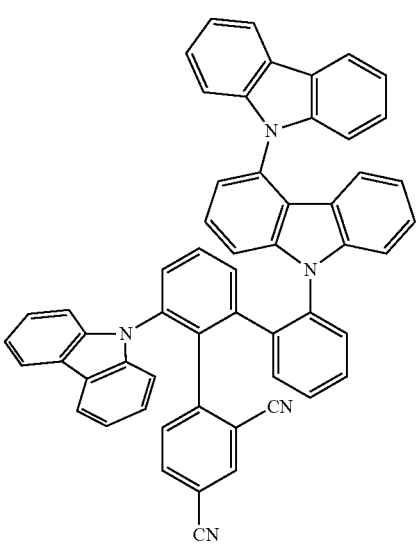

T-42
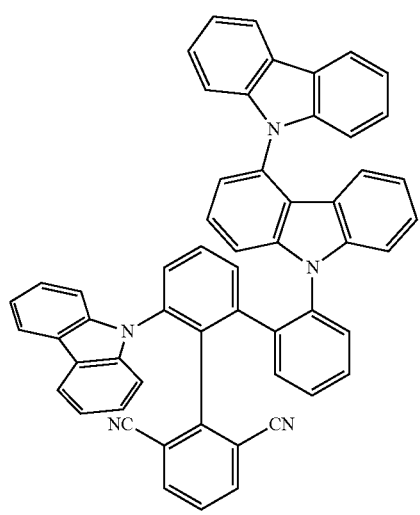
T-43
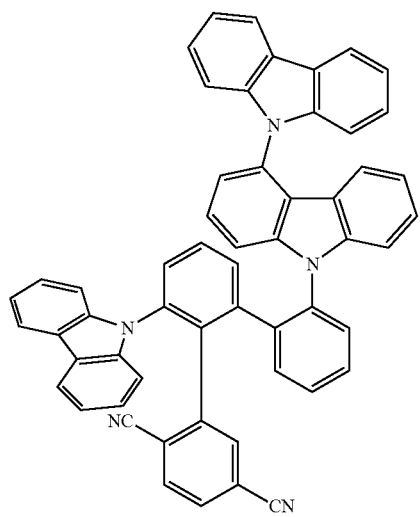
T-44
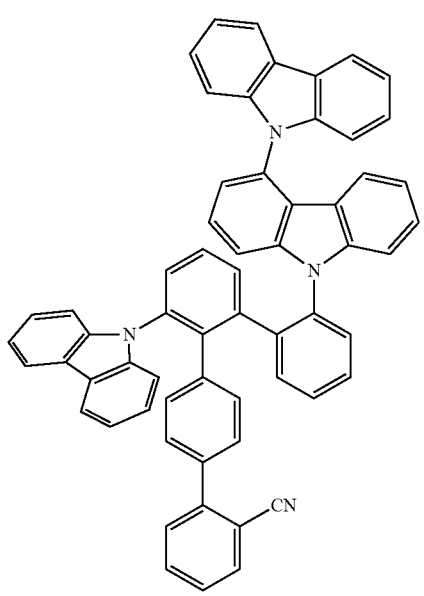
T-45
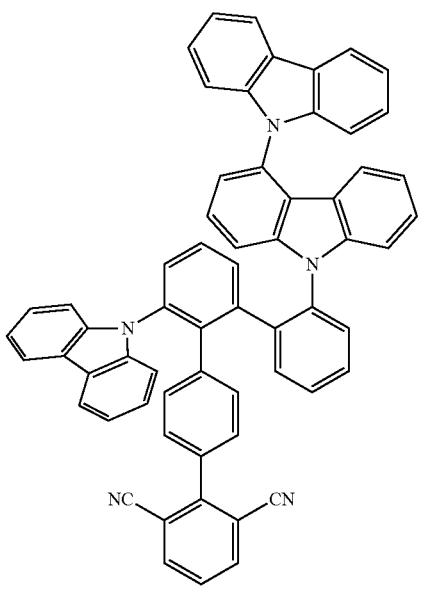
T-46
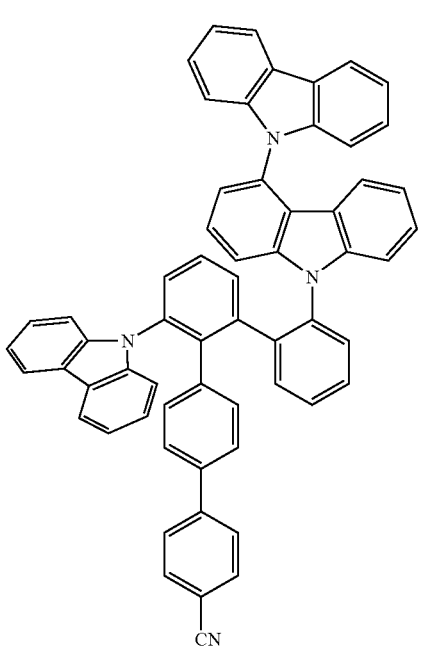

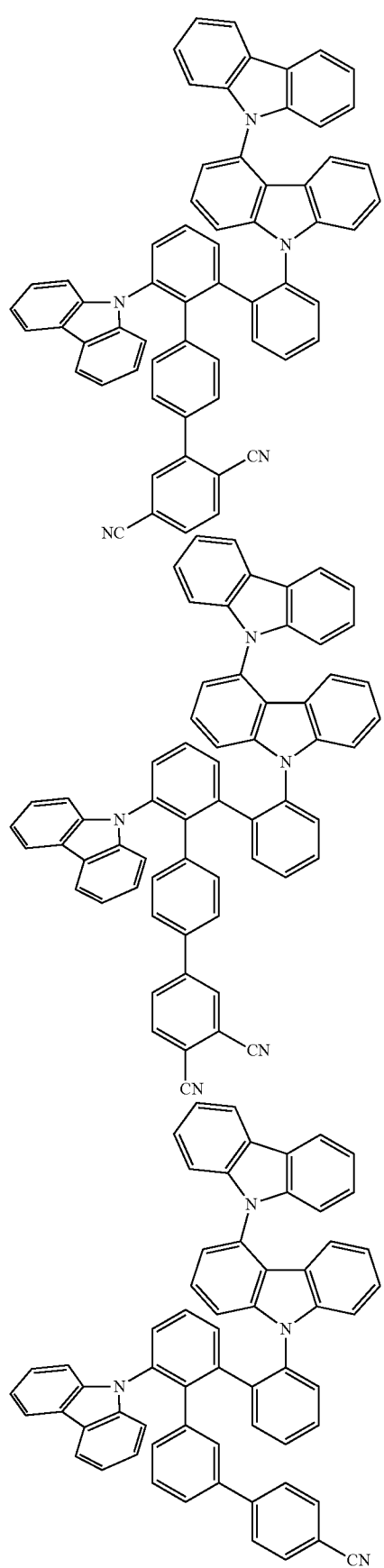
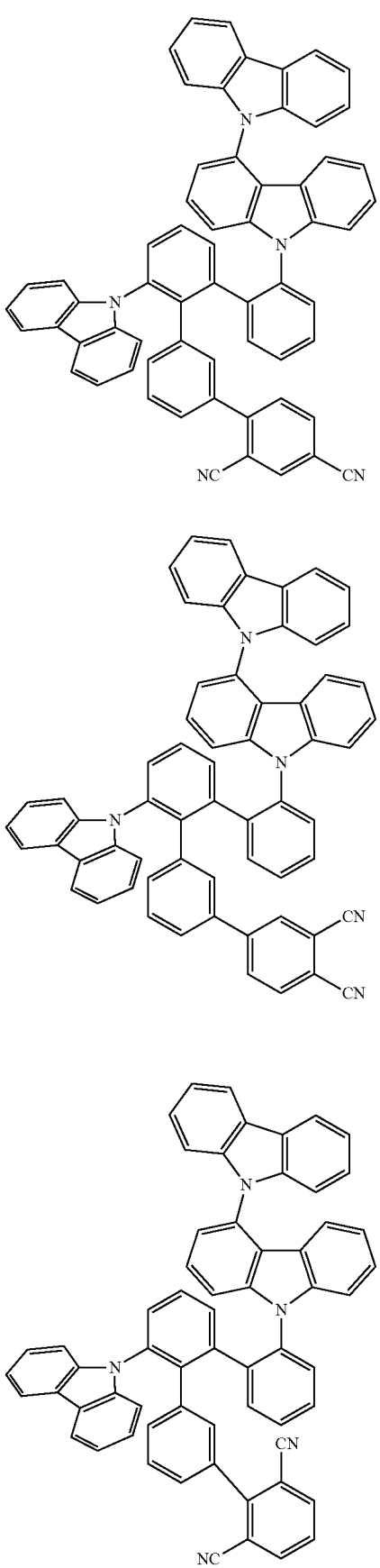

T-53
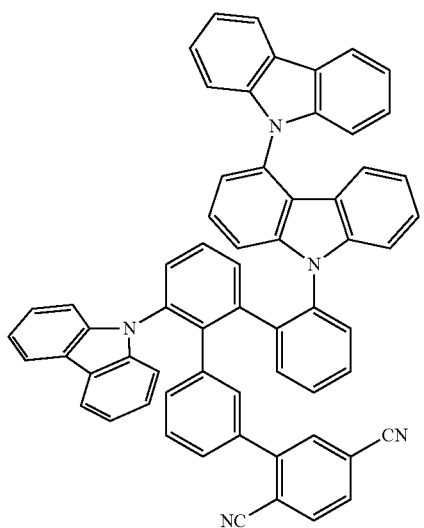

T-54
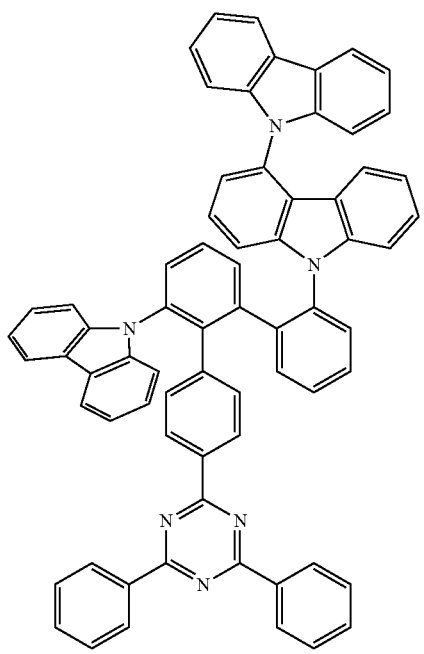

T-55
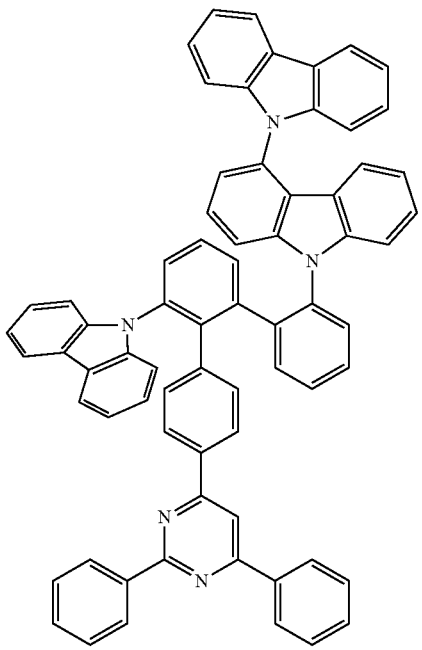

T-56
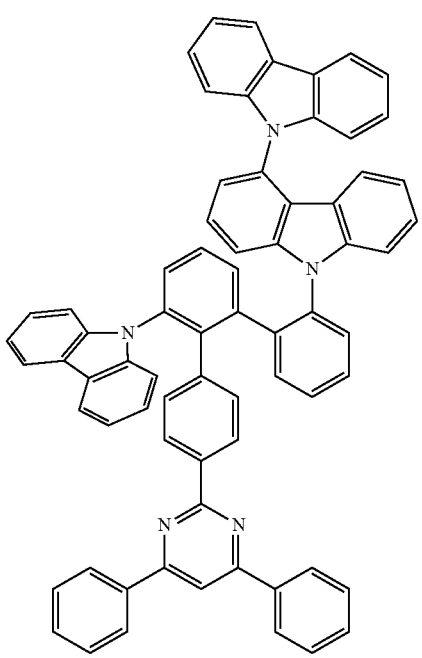

In the heterocyclic compound according to an embodiment of the present disclosure, an electron receiving part and a hole receiving part are separated in a molecule, while being orthogonally disposed. Accordingly, a difference between a singlet energy level (S1) and a triplet energy level (T1) may be close to 0. Therefore, efficiency (e.g., the light emitting efficiency) may be improved, and emission color may shift to short wavelengths. Therefore, deep blue emission may be realized.

In addition, the heterocyclic compound according to an embodiment of the present disclosure includes two carbazole groups, and the two carbazole groups are each connected to a respective benzene ring, and the hole receiving burden is distributed (e.g., between the two carbazole groups). Since the two carbazole groups are positioned at an ortho position and a meta position with respect to the biphenyl group, it is hard to influence onto each other (e.g., the two carbazole groups are sufficiently separated from each other). Accordingly, the two carbazole groups contribute to the increase of life (e.g., lifespan) of an organic electroluminescence device including the same.

The heterocyclic compound according to an embodiment of the present disclosure may be utilized as a luminescent material of an organic electroluminescence device, and for example, as a material for thermally activated delayed fluorescence. The heterocyclic compound according to an embodiment of the present disclosure may accomplish blue emission, for example, deep blue emission with high efficiency and long life.

Hereinafter, an organic electroluminescence device according to an embodiment of the inventive step will be explained. The explanation will be mainly with the difference in the heterocyclic compound according to an embodiment of the present disclosure, and the same description about the heterocyclic compound according to an embodiment of the present disclosure will not be repeated.

The organic electroluminescence device according to an embodiment of the present disclosure includes the above-described heterocyclic compound according to an embodiment of the present disclosure.

Figure 2:
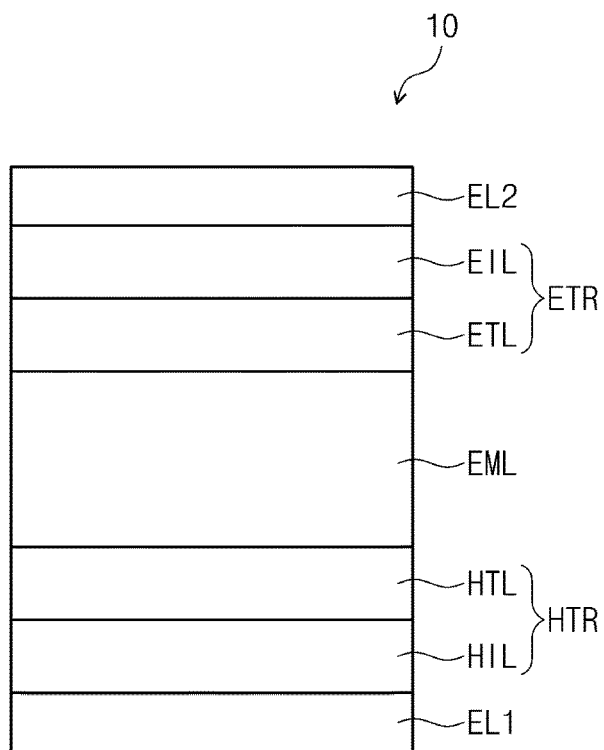
FIG. 2 is a cross-sectional view schematically illustrating an organic electroluminescence device according to an embodiment of the present disclosure.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure.

Referring to FIGS. 1 and 2, an organic electroluminescence device 10 according to an embodiment of the present disclosure may include a first electrode EL1, a hole transport region HTR, an emission layer EML, an electron transport region ETR, and a second electrode EL2.

The first electrode EL1 has conductivity (e.g., electrical conductivity). The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may be formed utilizing a transparent metal oxide such as indium tin oxide (ITO), indium zinc oxide (IZO), zinc oxide (ZnO), or indium tin zinc oxide (ITZO). If the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer and/or transflective layer formed utilizing the above materials, or a transparent layer formed utilizing ITO, IZO, ZnO, or ITZO. For example, the first electrode EL1 may have a three-layer structure of ITO/Ag/ITO, but an embodiment of the present disclosure is not limited thereto.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may be a single layer formed utilizing a single material, a single layer formed utilizing a plurality of different materials, or have a multi-layer structure including a plurality of layers formed utilizing a plurality of different materials.

For example, the hole transport region HTR may have the structure of a single layer, such as a hole injection layer HIL or a hole transport layer HTL. In addition, the hole transport region HTR may have a structure of a single layer formed utilizing a plurality of different materials, for example, a structure of a single layer formed utilizing a hole injection material and a hole transport material. In another embodiment, the hole transport region may have a multilayered structure laminated one by one from the first electrode EL1 to have the structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer. However, embodiments of the present disclosure are not limited thereto.

The hole transport region HTR may be formed utilizing various suitable methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, carbazole derivatives (such as N-phenyl carbazole and/or polyvinyl carbazole). Fluorine-based derivatives, N,N'-bis (3-methylphenyl)-N,N'-diphenyl[1,1-biphenyl]-4,4'-diamine (TPD), triphenylamine-based derivatives such as 4,4', 4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl) benzenamine] (TAPC), 4,4'-bis[N,N'-(3-tolyl)amino]-3,3'-dimethylbiphenyl (HMTPD), etc., may be further included.

The thickness of the hole transport region HTR may be from about 100 Å to about 10,000 Å, for example, from about 100 Å to about 1,000 Å. If the hole transport region HTR includes both the hole injection layer HIL and the hole transport layer HTL, the thickness of the hole injection layer HIL may be, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without the substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, however, embodiments of the present disclosure are not limited thereto. For example, non-limiting examples of the p-dopant may include quinone derivatives (such as tetracyanoquinodimethane (TCNQ), and 2,3,5,6-tetrafluoro-tetracyanoquinodimethane (F4-TCNQ)), and metal oxides (such as tungsten oxide, and molybdenum oxide). However, embodiments of the present disclosure are not limited thereto.

As described above, the hole transport region HTR may further include one of the hole buffer layer or the electron blocking layer other than the hole injection layer HIL and the hole transport layer HTL. The hole buffer layer may compensate an optical resonance distance according to the wavelength of light emitted from the emission layer EML and increase light emission efficiency. Materials included in the hole transport region HTR may be utilized as materials included in the hole buffer layer. The electron blocking layer is a layer preventing electron injection from the electron transport region ETR to the hole transport region HTR.

The emission layer EML is provided on the hole transport region HTR. The emission layer EML may have a thickness of, for example, about 100 Å to about 1,000 Å, or about 100 Å to about 300 Å. The emission layer EML may be a single layer formed utilizing a single material, a single layer formed utilizing a plurality of different materials, or may have a multilayer structure having a plurality of layers formed utilizing a plurality of different materials.

Hereinafter, an embodiment including the heterocyclic compound according to an embodiment of the present disclosure in the emission layer EML will be explained. However, an embodiment of the present disclosure is not limited thereto. The heterocyclic compound according to an embodiment of the present disclosure may be included in at least one organic layer provided between the first electrode EL1 and the second electrode EL2. For example, the heterocyclic compound according to an embodiment of the present disclosure may be included in the hole transport layer HTL. For example, the heterocyclic compound according to an embedment of the present disclosure may be included in the hole transport layer HTL, which makes contact with the emission layer EML.

The emission layer EML may include the heterocyclic compound according to an embodiment of the present disclosure. Particularly, the emission layer EML may include a heterocyclic compound represented by Formula 1 below.

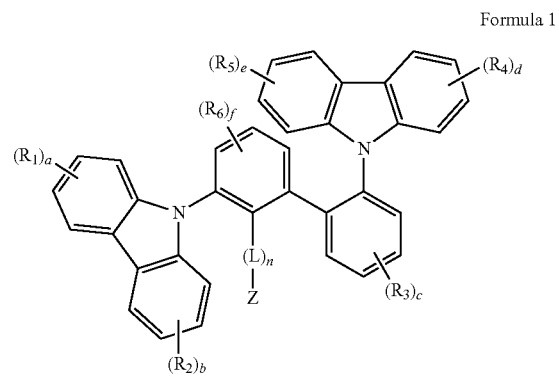

Formula 1

In Formula 1, explanation on $R_1$ to $R_6$, a to f, n, L and Z is the same as described above. For example, Z may be represented by Formula 2-1 or Formula 2-2 below.

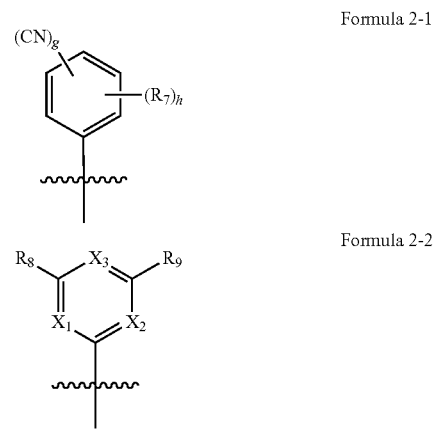

Formula 2-1

Formula 2-2

In Formula 2, explanation on $R_7$ to $R_9$, g, and $X_1$ to $X_3$ is the same as described above and will not be repeated.

The emission layer EML may include one, two, or more of the heterocyclic compounds represented by Formula 1. The emission layer EML may further include a suitable (e.g., a known) material in addition to the heterocyclic compound represented by Formula 1. For example, a fluorescent material including any one selected from spiro-DPVBi, 2,2',7,7'-tetrakis(biphenyl-4-yl)-9,9'-spirobifluorene (spiro-6P, spiro-sexiphenyl), distyryl-benzene (DSB), distyryl-arylene (DSA), a polyfluorene (PFO)-based polymer, and a poly(p-phenylene vinylene) (PPV)-based polymer may be further included. However, an embodiment of the present disclosure is not limited thereto.

The emission layer EML may include the heterocyclic compound according to an embodiment of the present disclosure as a luminescent material and may emit thermally activated delayed fluorescence.

The heterocyclic compound according to an embodiment of the present disclosure may be a material for thermally activated delayed fluorescence, which emits blue light. The heterocyclic compound according to an embodiment of the present disclosure may emit blue light having a wavelength (e.g., a wavelength region) of less than about 470 nm, for example, may emit deep blue light having a wavelength region of about 440 nm to about 470 nm, or about 450 nm to about 470 nm.

As described above, the heterocyclic compound according to an embodiment of the present disclosure has an absolute value of a difference between a singlet energy level and a triplet energy level of about 0.2 eV or less. By controlling a singlet-triplet energy gap small, efficiency in emitting thermally activated delayed fluorescence may be enhanced.

The emission layer EML may further include a host. The host may include a commonly utilized suitable material, for example, tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalen-2-yl) anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane (DPSiO3), octaphenylcyclotetra siloxane (DPSiO4), 2,8-bis(diphenylphosphoryl)dibenzofuran (PPF), etc. However, embodiments of the present disclosure are not limited thereto.

The electron transport region ETR is provided on the emission layer EML. The electron transport region ETR may include at least one of a hole blocking layer, an electron transport layer ETL, or an electron injection layer EIL. However, embodiments of the present disclosure are not limited thereto.

The electron transport region ETR may be a single layer formed utilizing a single material, a single layer formed utilizing a plurality of different materials, or may have a multilayer structure including a plurality of layers formed utilizing a plurality of different materials.

For example, the electron transport region ETR may have the structure of a single layer such as an electron injection layer EIL or an electron transport layer ETL. In addition, the electron transport region ETR may have a single layer structure formed utilizing a plurality of different materials, for example, a single layer structure formed utilizing an electron injection material and an electron transport material. In another embodiment, the electron transport region may have a multiplayer structure laminated one by one from the first electrode EL1 to form the structure of electron transport layer ETL/electron injection layer EIL, or hole blocking layer/electron transport layer ETL/electron injection layer EIL. However, embodiments of the present disclosure are not limited thereto. The thickness of the electron transport region ETR may be, for example, from about 1,000 Å to about 1,500 Å.

The electron transport region ETR may be formed utilizing various suitable methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl) anthracene (ADN), or a mixture thereof. However, embodiments of the present disclosure are not limited thereto. The thickness of the electron transport layer ETL may be from about 100 Å to about 1,000 Å, for example, from about 150 Å to about 500 Å. If the thickness of the electron transport layer ETL satisfies the above-described ranges, satisfactory electron transport properties may be obtained without the substantial increase of a driving voltage.

If the electron transport region ETR includes the electron injection layer EIL, the electron transport region ETR may include LiF, lithium quinolate (LiQ), Li$_2$O, BaO, NaCl, CsF, a metal in lanthanoides such as Yb, or a metal halide such as RbCl and RbI. However, embodiments of the present disclosure are not limited thereto. The electron injection layer EIL also may be formed utilizing a mixture material of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layer EIL may be from about 1 Å to about 100 Å, or from about 3 Å to about 90 Å. If the thickness of the electron injection layer EIL satisfies the above described ranges, satisfactory electron injection properties may be obtained without inducing the substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer and/or a transflective layer formed utilizing the above-described materials, or a transparent conductive layer formed utilizing ITO, IZO, ZnO, ITZO, etc.

Even not shown, the second electrode EL2 may be connected with an auxiliary electrode. If the second electrode EL2 is connected with the auxiliary electrode, the resistance of the second electrode EL2 may be decreased.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and the excitons may emit light via transition from an excited state to a ground state.

If the organic electroluminescence device 10 is a top emission device, the first electrode EL1 may be a reflective electrode, and the second electrode EL2 may be a transmissive electrode or a transflective electrode. If the organic electroluminescence device 10 is a bottom emission device, the first electrode EL1 may be the transmissive electrode or the transflective electrode, and the second electrode EL2 may be the reflective electrode.

The organic electroluminescence device according to an embodiment of the present disclosure includes the heterocyclic compound represented by Formula 1 and may accomplish the improvement of lifespan, efficiency, and blue emission (for example, deep blue emission) at the same time.

Hereinafter, the present disclosure will be explained in more detail referring to preferred embodiments and comparative embodiments. The following embodiments are only for illustration purpose to assist the understanding of the present disclosure. However, the scope of the present disclosure is not limited thereto.

Synthetic Examples

The heterocyclic compound according to an embodiment of the present disclosure may be synthesized, for example, as follows. However, the synthetic method of the heterocyclic compound according to an embodiment of the present disclosure is not limited thereto.

1. Synthesis of Compound T-04

Compound T-04, which is a heterocyclic compound according to an embodiment of the present disclosure, may be synthesized, for example, by the following reaction:

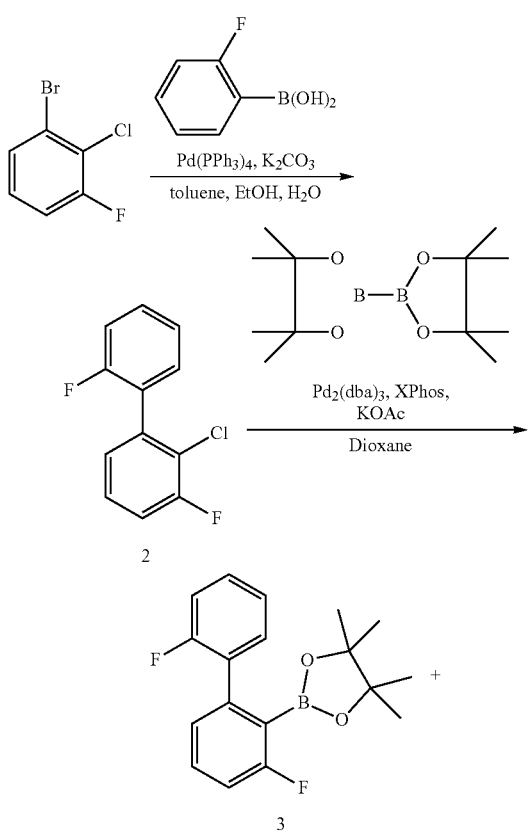

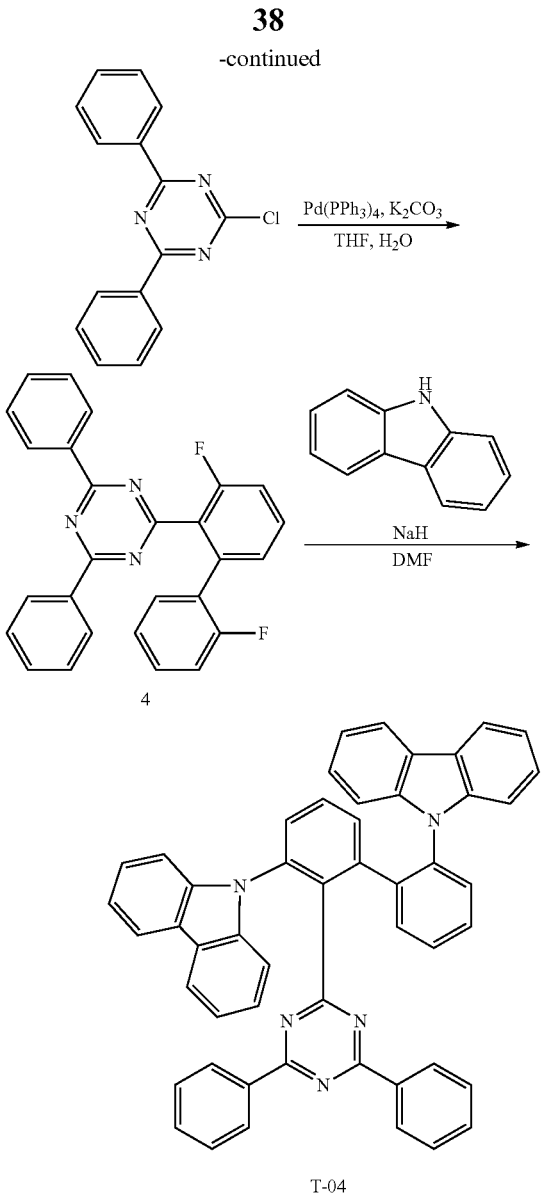

(Synthesis of Intermediate 2)

Under an argon (Ar) atmosphere, 4.00 g of 1-bromo-2-chloro-3-fluorobenzene, 5.99 g of 2-fluorophenylboron acid, 7.92 g of $K_2CO_3$, and 100 ml of a mixture solution of toluene/EtOH/water (7:1:2) in which 1.67 g of $Pd(PPh_3)_4$ was dissolved were heated and stirred at about 80° C. for about 5 hours in a 300 ml, three-neck flask. After cooling in the air, dichloromethane was added, an organic layer was separated and taken, and the solvents were removed. The crude product thus obtained was separated by silica gel chromatography to obtain 4.62 g (yield 72%) of Intermediate 2 as a clear oil.

The molecular weight of Intermediate 2 measured by FAB-MS was 224.

(Synthesis of Intermediate 3)

Under an argon (Ar) atmosphere, 4.00 g of Intermediate 2, 10.9 g of bis(pinacolato)diboron, 5.24 g of KOAc, and 23 ml of a dioxane solution in which 0.67 g of $Pd_2(dba)_3$ were dissolved, were heated and stirred at about 110° C. for about 5 hours in a 300 ml, three-neck flask. After cooling in the air, dichloromethane was added, an organic layer was separated and taken, and the solvents were removed. The crude product thus obtained was separated by silica gel chromatography to obtain 4.56 g (yield 81%) of Intermediate 3 as a clear oil.

The molecular weight of Intermediate 3 measured by FAB-MS was 316.

(Synthesis of Intermediate 4)

Under an argon (Ar) atmosphere, 1.50 g of 2-chloro-4,6-diphenyl-1,3,5-triazine, 1.89 g of Intermediate 3, 1.55 g of $K_2CO_3$, and 80 ml of a mixture solution of toluene/EtOH/water (7:1:2) in which 0.39 g of $Pd(PPh_3)_4$ was dissolved, were heated and stirred at about 80° C. for about 5 hours in a 200 ml, three-neck flask. After cooling in the air, dichloromethane was added, an organic layer was separated and taken, and the solvents were removed. The crude product thus obtained was separated by silica gel chromatography to obtain 2.05 g (yield 87%) of Intermediate 4 as a clear oil.

The molecular weight of Intermediate 4 measured by FAB-MS was 421.

(Synthesis of Compound T-04)

Under an argon (Ar) atmosphere, 1.40 g of carbazole, 1.60 g of Intermediate 4, and 93 ml of a DMF solution in which 0.23 g of NaH was dissolved were heated and stirred at about 120° C. for about 5 hours in a 200 ml, three-neck flask. After cooling in the air, a precipitate was filtered, washed with water, and EtOH and toluene, and recrystallized with toluene/EtOH to obtain 2.17 g (yield 80%) of Compound T-04 as a pale yellow solid.

The molecular weight of Compound T-04 measured by FAB-MS was 715.

$^1$H NMR (CDCl$_3$, 25° C., 300 Hz) δ=9.18 (d, J=9.0 Hz, 2H), 8.92-8.86 (m, 6H), 8.75 (d, J=8.5 Hz, 4H), 8.33 (d, J=8.5 Hz, 2H), 7.96 (d, J=8.5 Hz, 2H), 7.86-7.80 (m, 5H), 7.76-7.70 (m, 3H), 7.55 (d, J=8.5 Hz, 4H), 7.50-7.44 (m, 3H), 7.37-7.34 (m, 3H).

2. Synthesis of Compound T-14

Compound T-14 was synthesized by conducting the same method for synthesizing Compound T-04 except for utilizing 2-bromo-1,3-benzenedicarbonitrile instead of 2-chloro-4,6-diphenyl-1,3,5-triazine.

The molecular weight of Compound T-14 measured by FAB-MS was 611.

$^1$H NMR (CDCl$_3$, 25° C., 300 Hz) δ=9.10 (d, J=9.0 Hz, 2H), 8.33-8.14 (m, 6H), 7.96 (d, J=8.5 Hz, 2H), 7.86-7.80 (m, 5H), 7.68-7.61 (m, 3H), 7.55 (d, J=8.5 Hz, 2H), 7.51-7.46 (m, 3H), 7.39-7.35 (m, 3H).

3. Synthesis of Compound T-17

Compound T-17 was synthesized by conducting the same method for synthesizing Compound T-04 except for utilizing 4'-bromo-[1,1'-biphenyl]-2,6-dicarbonitrile instead of 2-chloro-4,6-diphenyl-1,3,5-triazine.

The molecular weight of Compound T-17 measured by FAB-MS was 738.

$^1$H NMR (CDCl$_3$, 25° C., 300 Hz) δ=9.10 (d, J=9.0 Hz, 2H), 8.33-8.14 (m, 6H), 8.00 (d, J=8.7 Hz, 4H), 7.96 (d, J=8.5 Hz, 2H), 7.86-7.80 (m, 5H), 7.76-7.71 (m, 3H), 7.56 (d, J=8.5 Hz, 2H), 7.40-7.34 (m, 3H), 7.22-7.10 (m, 3H).

4. Synthesis of Compound T-26

Compound T-26 was synthesized by conducting the same method for synthesizing Compound T-04 except for utilizing 2-(4-bromophenyl)-4,6-diphenyl-1,3,5-triazine instead of 2-chloro-4,6-diphenyl-1,3,5-triazine.

The molecular weight of Compound T-26 measured by FAB-MS was 792.

$^1$H NMR (CDCl$_3$, 25° C., 300 Hz) δ=9.16 (d, J=9.0 Hz, 2H), 8.95-8.85 (m, 6H), 8.64 (d, J=8.5 Hz, 4H), 8.33 (d, J=8.5 Hz, 2H), 7.96 (d, J=8.5 Hz, 2H), 7.86-7.80 (m, 5H), 7.74-7.60 (m, 7H), 7.55 (d, J=8.5 Hz, 4H), 7.51-7.44 (m, 3H), 7.37-7.34 (m, 3H).

5. Synthesis of Compound T-32

Compound T-32 was synthesized by conducting the same method for synthesizing Compound T-04 except for utilizing 3,9'-bi-9H-carbazole instead of carbazole.

The molecular weight of Compound T-32 measured by FAB-MS was 1045.

$^1$H NMR (CDCl$_3$, 25° C., 300 Hz) δ=8.80 (d, J=9.0 Hz, 2H), 8.43-8.32 (m, 9H), 8.20 (d, J=9.0 Hz, 4H), 7.99 (d, J=8.7 Hz, 2H), 7.86-7.81 (m, 9H), 7.66-7.51 (m, 3H), 7.46 (d, J=8.8 Hz, 2H), 7.38-7.34 (m, 3H), 7.22-7.10 (m, 3H).

6. Synthesis of Compound T-37

Compound T-37 was synthesized by conducting the same method for synthesizing Compound T-04 except for utilizing 4,9'-bi-9H-carbazole instead of carbazole.

The molecular weight of Compound T-37 measured by FAB-MS was 1045.

$^1$H NMR (CDCl$_3$, 25° C., 300 Hz) δ=8.90 (d, J=9.0 Hz, 2H), 8.63-8.52 (m, 9H), 8.31 (d, J=8.7 Hz, 4H), 8.21 (d, J=8.7 Hz, 2H), 7.91-7.71 (m, 9H), 7.63-7.50 (m, 3H), 7.46 (d, J=8.8 Hz, 2H), 7.38-7.34 (m, 3H), 7.24-7.15 (m, 3H).

Device Manufacturing Examples

Organic electroluminescence devices of Examples 1 to 6 were manufactured utilizing Compounds T-04, T-14, T-17, T-26, T-32 and T-37 as the emission layer materials.

Example Compounds

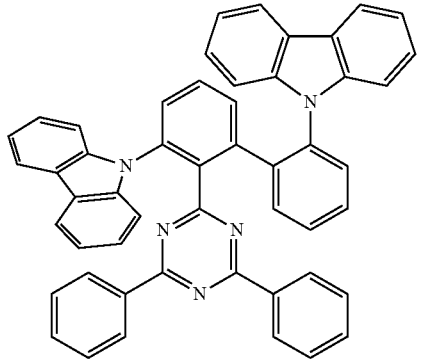

T-04

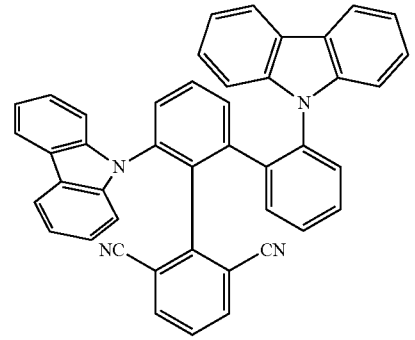

T-14

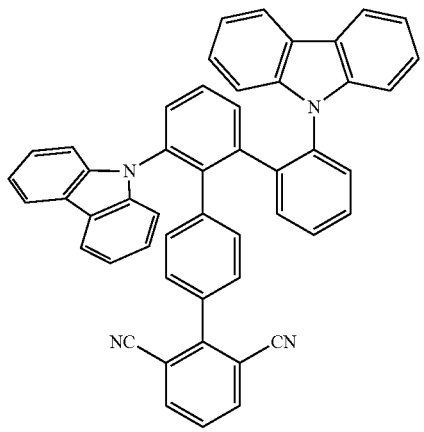 T-17
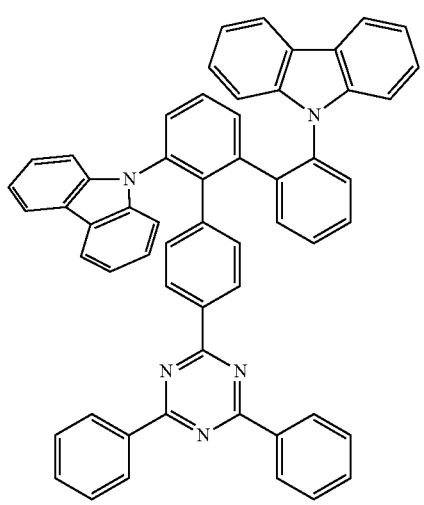 T-26
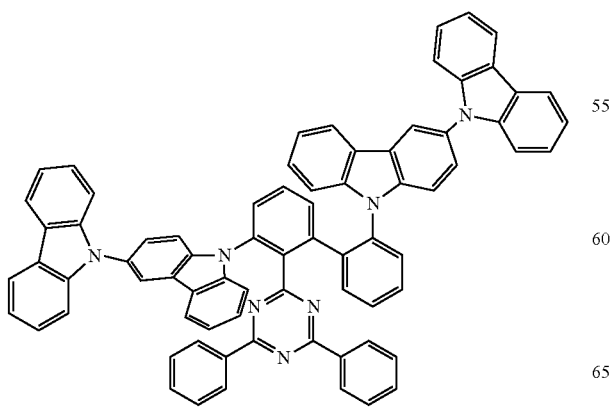 T-32
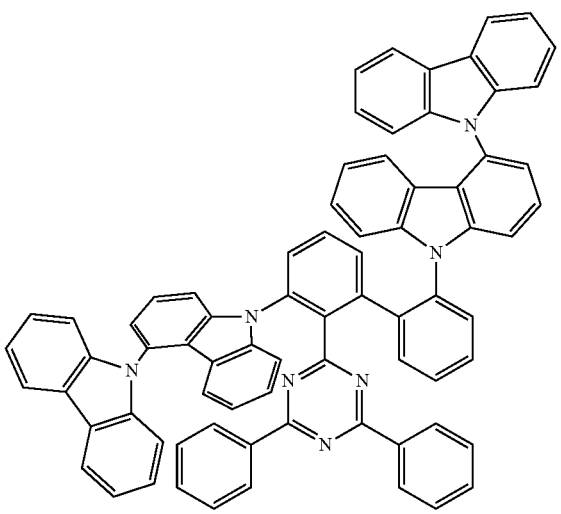 T-37
Organic electroluminescence devices of Comparative Examples 1 to 7 were manufactured utilizing Comparative Compounds E-1 to E-7 as the emission layer materials.
Comparative Compounds
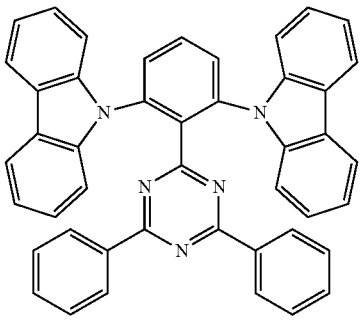 E-1
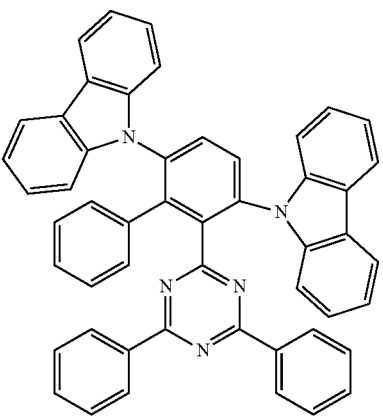 E-2

-continued

E-3
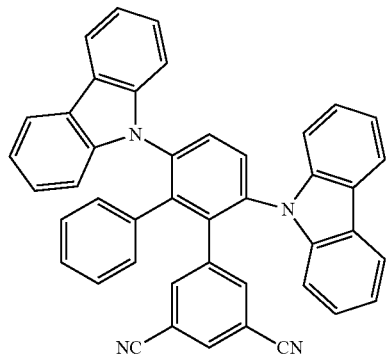

E-4
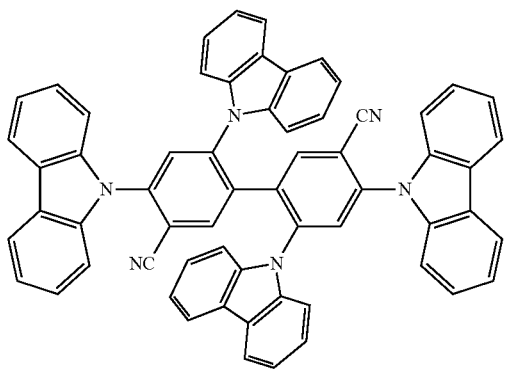

E-5
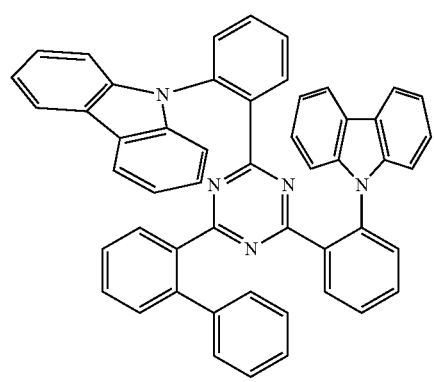

E-6
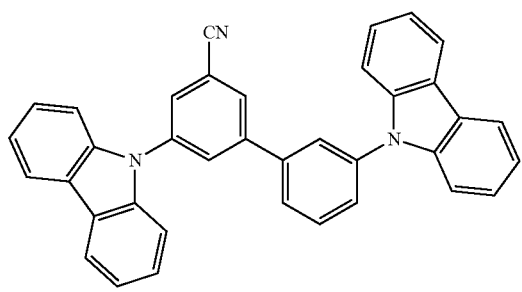

E-7
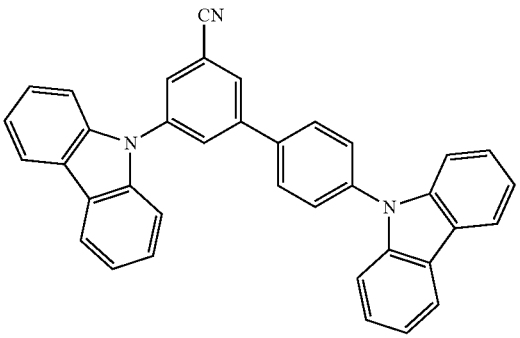

The organic electroluminescence devices of Examples 1 to 6 and Comparative Examples 1 to 7 were manufactured as follows. A first electrode with a thickness of about 100 nm was formed utilizing ITO, a hole injection layer with a thickness of about 10 nm was formed utilizing HAT-CN, a hole transport layer with a thickness of about 80 nm was formed utilizing α-NPD, an electron blocking layer with a thickness of about 5 nm was formed utilizing mCP, an emission layer with a thickness of about 20 nm was formed utilizing bis{2-[di(phenyl) phosphino]phenyl}ether oxide (DPEPO) doped with 20% of the respective example compound or comparative compound, a hole blocking layer with a thickness of about 10 nm was formed utilizing DPEPO, an electron transport layer with a thickness of about 30 nm was formed utilizing TPBi, an electron injection layer with a thickness of about 0.5 nm was formed utilizing LiF, and a second electrode with a thickness of about 100 nm was formed utilizing Al. Each layer was formed by a vacuum deposition method.

TABLE 1

| | Emission layer dopant | $\lambda$max (nm) | EQE (%) | Life LT50 (h) |
|---|---|---|---|---|
| Example 1 | Example Compound T-04 | 455 | 18.5 | 31.5 |
| Example 2 | Example Compound T-14 | 458 | 18.0 | 28.0 |
| Example 3 | Example Compound T-17 | 462 | 17.0 | 29.0 |
| Example 4 | Example Compound T-26 | 465 | 18.0 | 30.0 |
| Example 5 | Example Compound T-32 | 464 | 17.5 | 28.0 |
| Example 6 | Example Compound T-37 | 463 | 17.0 | 30.0 |
| Comparative Example 1 | Comparative Compound E-1 | 455 | 12.5 | 10.0 |
| Comparative Example 2 | Comparative Compound E-2 | 470 | 11.5 | 12.0 |
| Comparative Example 3 | Comparative Compound E-3 | 472 | 10.5 | 12.5 |
| Comparative Example 4 | Comparative Compound E-4 | 460 | 12.5 | 13.5 |
| Comparative Example 5 | Comparative Compound E-5 | 475 | 10.5 | 15.5 |
| Comparative Example 6 | Comparative Compound E-6 | 459 | 12.0 | 13.5 |
| Comparative Example 7 | Comparative Compound E-7 | 463 | 11.0 | 15.5 |

In Table 1, $\lambda$max (nm) represents the maximum wavelength of light emitted by the organic electroluminescence device, EQE (%) represents the external quantum efficiency of the organic electroluminescence device, and Life LT50 represents the lifespan of the organic electroluminescence device.

Referring to Table 1, the organic electroluminescence devices according to Examples 1 to 6 were found to emit deep blue light and attained increased efficiency and life (e.g., lifespan) when compared to the organic electroluminescence devices according to Comparative Examples 1 to 7. Since an electron accepting part and a hole accepting part are separated and are orthogonal to each other in the example compounds, a difference between a singlet energy level and a triplet energy level in a high EQE approaches 0, and efficiency is improved, and the wavelength of emission color is shortened. In addition, the example compounds have a structure in which one carbazole group is substituted at one benzene ring (i.e., each benzene ring is substituted with a single substituted or unsubstituted carbazole group), and the hole accepting burden is distributed to increase the life of a device.

Meanwhile, in Comparative Examples 1 to 4, two carbazole groups are substituted at one benzene ring, and the hole accepting burden is large (e.g., the hole accepting burden is concentrated), and thus, life is short. Particularly, in Comparative Example 1, the structure is sterically very complicated, and is more likely to be decomposed, and thus, life is short. In Comparative Examples 5 to 7, twist of a carbazole group is small and a difference between a singlet energy level and a triplet energy level is large, and thus, efficiency of a device is low, charge balance is lost and life is short.

The heterocyclic compound according to an embodiment of the present invention has a structure in which one (i.e., a single substituted or unsubstituted) carbazole group is directly substituted at one benzene ring, and the substitution position of the carbazole group is designed to have sufficient twist. Accordingly, the difference between a singlet energy level and a triplet energy level approaches 0, and the hole accepting burden is distributed. Accordingly, life and efficiency are improved. In addition, referring to the results of Table 1, the heterocyclic compound according to an embodiment of the present disclosure may accomplish deep blue emission as well as long life and excellent efficiency.

The compound according to an embodiment of the present disclosure may be utilized as a material for an organic electroluminescence device.

The compound according to an embodiment of the present disclosure may be utilized as a material for emitting thermally activated delayed fluorescence.

The organic electroluminescence device including the compound according to an embodiment of the present disclosure may accomplish excellent efficiency and life.

Although the exemplary embodiments of the present invention have been described, it is understood that the present invention should not be limited to these exemplary embodiments, but various changes and modifications can be made by one ordinary skilled in the art within the spirit and scope of the appended claims, and equivalents thereof.

What is claimed is:

1. A heterocyclic compound represented by Formula 1, wherein an absolute value of a difference between a singlet energy level and a triplet energy level of the heterocyclic compound is about 0.2 eV or less:

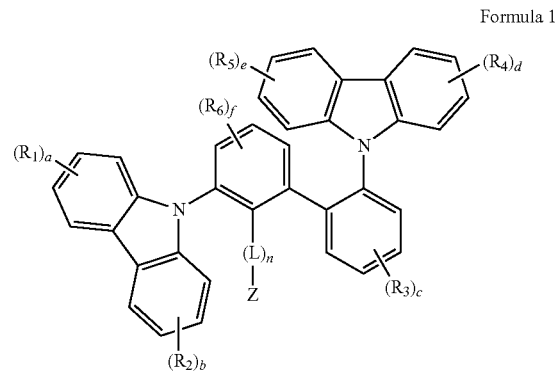

Formula 1 wherein, in Formula 1,
$R_1$ to $R_6$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
L is a substituted or unsubstituted arylene group having 6 to 30 carbon atoms for forming a ring, or a substituted or unsubstituted heteroarylene group having 2 to 30 carbon atoms for forming a ring,
a, b, c, d and e are each independently an integer of 0 to 4,
f is an integer of 0 to 3,
n is 0 or 1, and
Z is represented by Formula 2-1 or Formula 2-2:

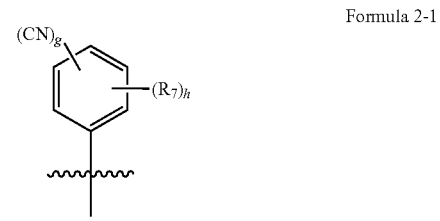

Formula 2-1

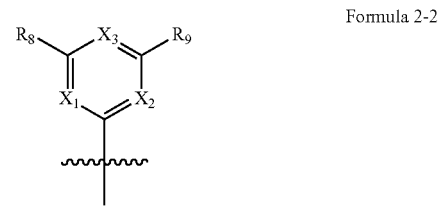

Formula 2-2 wherein, in Formula 2-1,
g is 1 or 2, when g is 1, h is an integer of 0 to 4, and when g is 2, h is an integer of 0 to 3, and
$R_7$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
wherein, in Formula 2-2,
$X_1$ to $X_3$ are each independently $CR_{10}$ or N,
at least one of $X_1$ to $X_3$ is N, and
$R_8$ to $R_{10}$ are each independently a hydrogen atom, deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, wherein when Z is represented by Formula 2-1, n is 1.

2. The heterocyclic compound of claim 1, wherein Z is represented by one of Formulae 3-1 to 3-9:

Formula 3-1
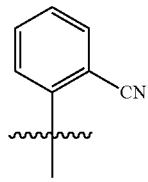

Formula 3-2
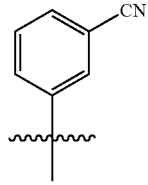

Formula 3-3
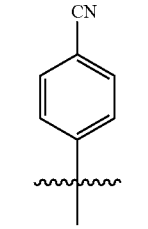

Formula 3-4
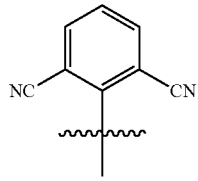

Formula 3-5
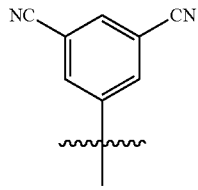

Formula 3-6
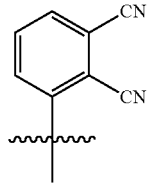

Formula 3-7
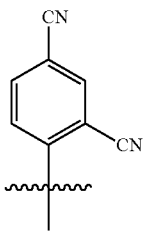

Formula 3-8
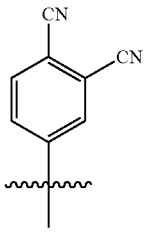

Formula 3-9
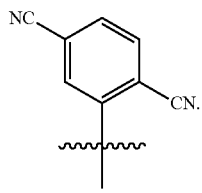

3. A heterocyclic compound represented by Formula 1, wherein an absolute value of a difference between a singlet energy level and a triplet energy level of the heterocyclic compound is about 0.2 eV or less:

Formula 1
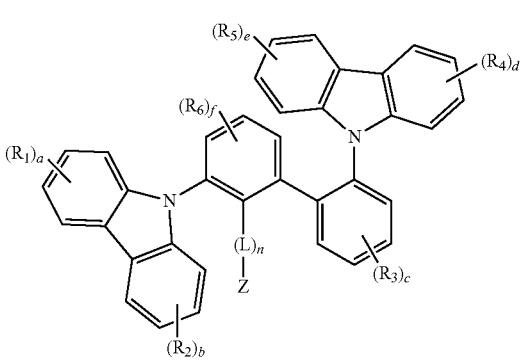

wherein, in Formula 1, $R_1$ to $R_6$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, L is a substituted or unsubstituted arylene group having 6 to 30 carbon atoms for forming a ring, or a substituted or unsubstituted heteroarylene group having 2 to 30 carbon atoms for forming a ring, a, b, c, d and e are each independently an integer of 0 to 4,
f is an integer of 0 to 3,
n is 0 or 1, and
Z is represented by Formula 2-1 or Formula 2-2:

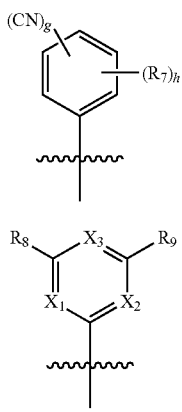

Formula 2-1

Formula 2-2 wherein, in Formula 2-1,
p is 1 or 2, when g is 1, h is an integer of 0 to 4, and when g is 2, h is an integer of 0 to 3, and
$R_7$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
wherein, in Formula 2-2,
$X_1$ to $X_3$ are each independently $CR_{10}$ or N,
at least one of $X_1$ to $X_3$ is N, and
$R_8$ to $R_{10}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
wherein Z is represented by Formula 2-2-1:

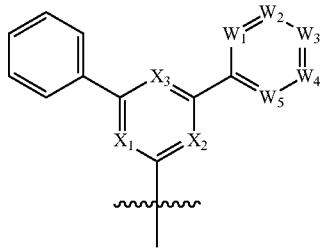

Formula 2-2-1 wherein, in Formula 2-2-1,
$W_1$ to $W_5$ are each independently CH or N, and
$X_1$ to $X_3$ are the same as defined above.

4. The heterocyclic compound of claim 3, wherein a total number of N in $W_1$ to $W_5$ is 0 or 1.

5. The heterocyclic compound of claim 1, wherein L is a substituted or unsubstituted phenylene group.

6. The heterocyclic compound of claim 1, wherein at least one of $R_1$, $R_2$, $R_4$, and $R_5$ is a substituted or unsubstituted phenyl group, or a substituted or unsubstituted carbazole group.

7. The heterocyclic compound of claim 6, wherein at least one of $R_1$, $R_2$, $R_4$, and $R_5$ is represented by one of following structures:

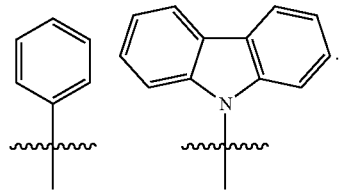

8. The heterocyclic compound of claim 1, wherein a+b+d+e is 0, 1 or 2.

9. The heterocyclic compound of claim 1, wherein the heterocyclic compound represented by Formula 1 is one selected from compounds represented in Compound Group 1:

[Compound Group 1]

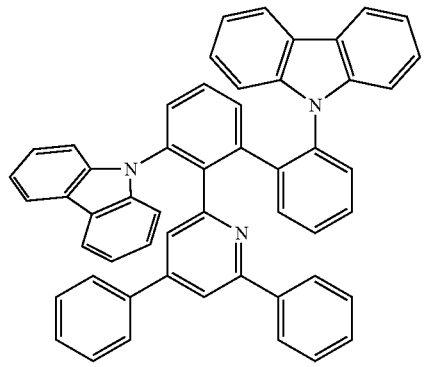

T-01

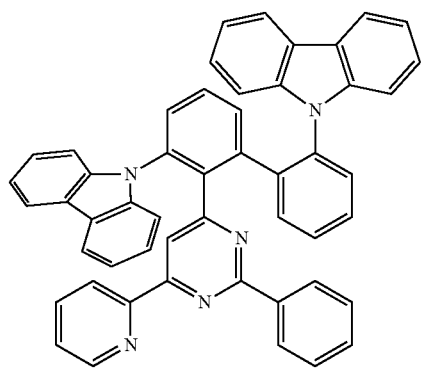

T-02

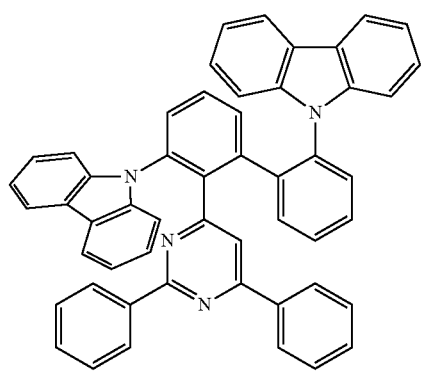

T-03

T-04 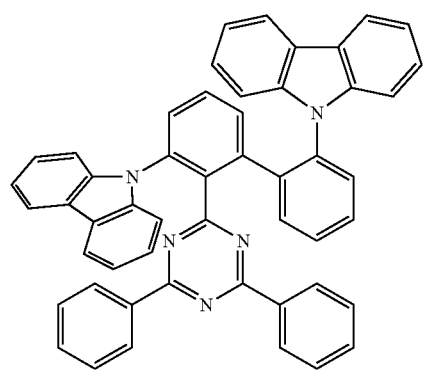
T-05 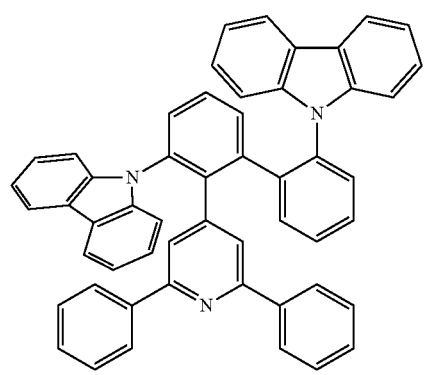
T-06 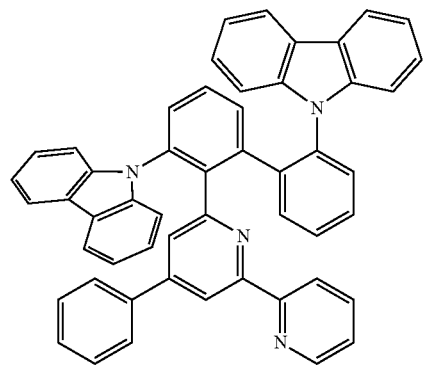
T-07 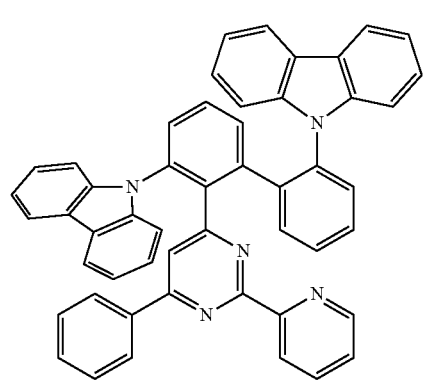
T-08 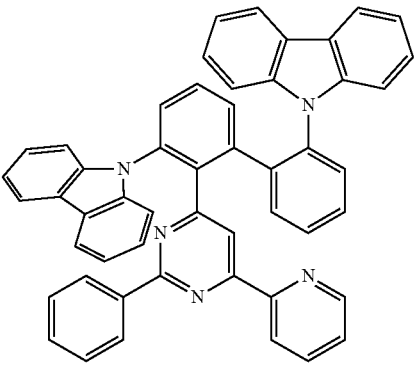
T-09 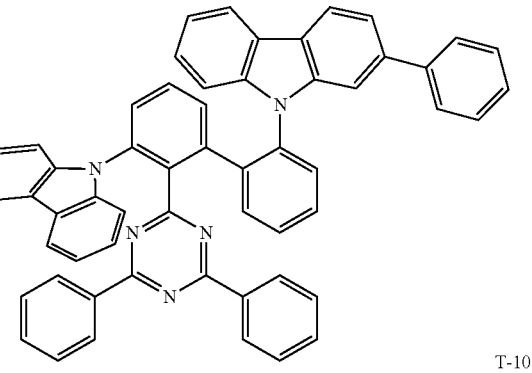
T-10 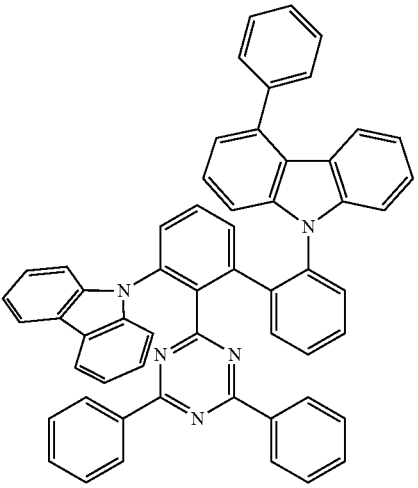
T-16 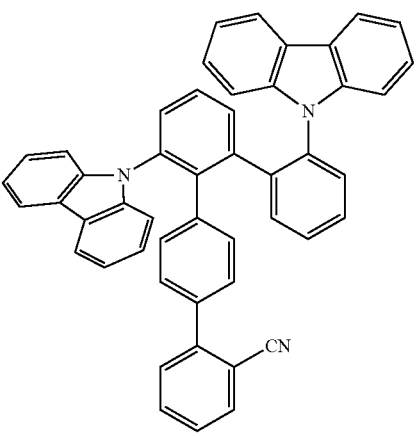

T-17
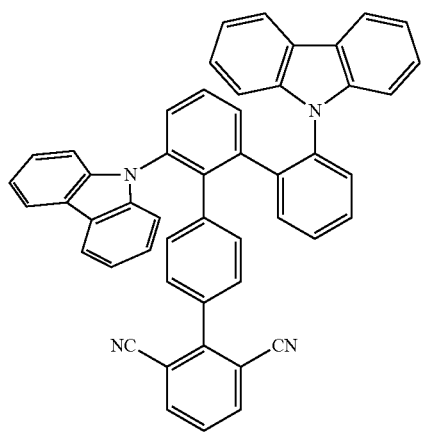
T-18
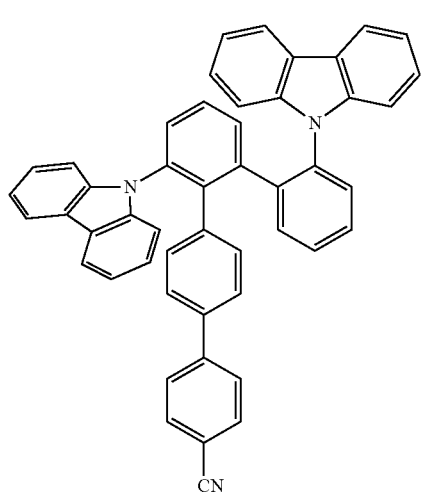
T-19
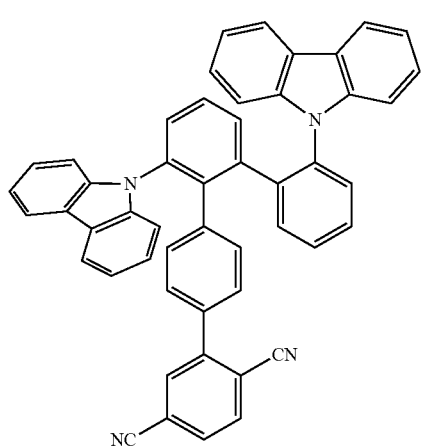
T-20
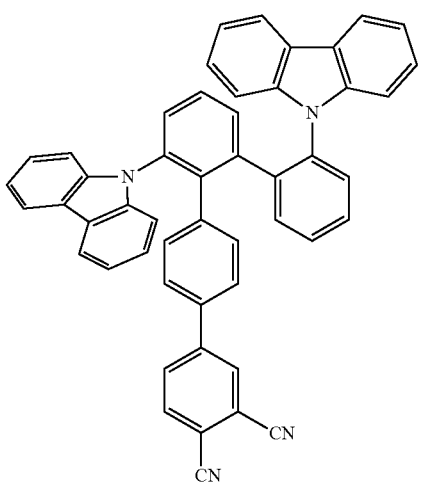
T-21
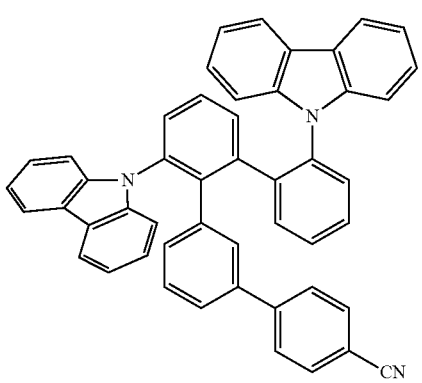
T-22
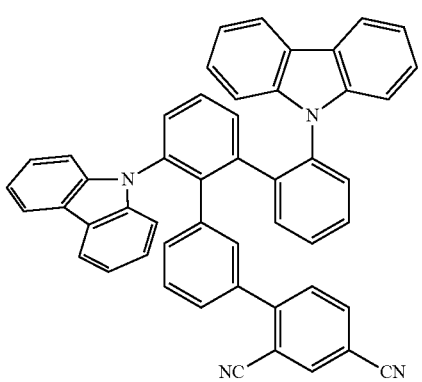
T-23
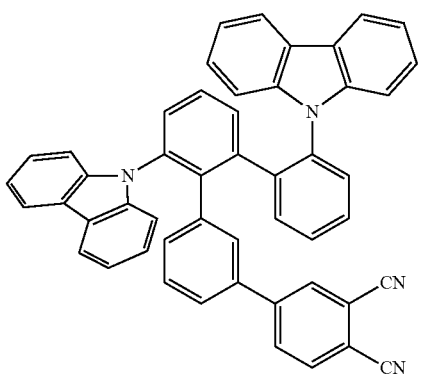

-continued
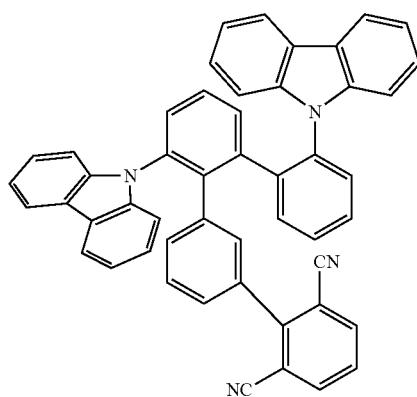
T-24
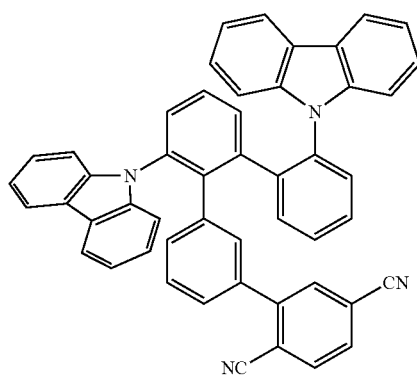
T-25
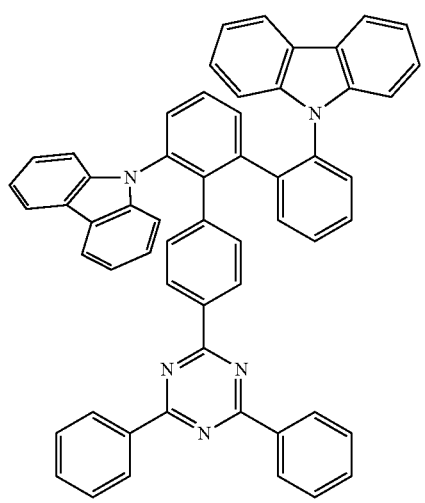
T-26
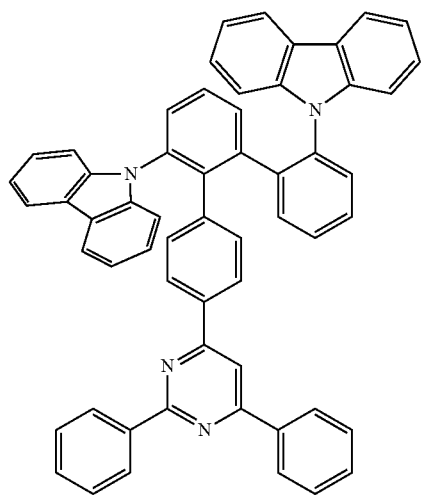
T-27
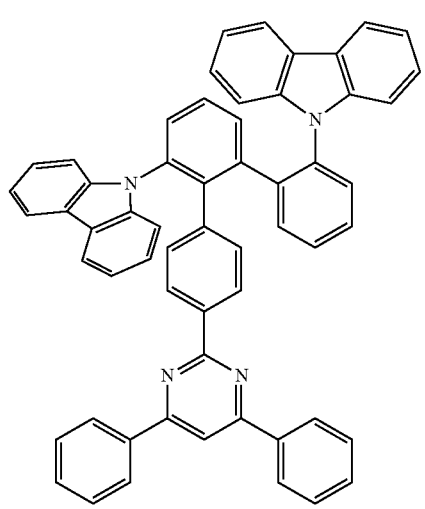
T-28
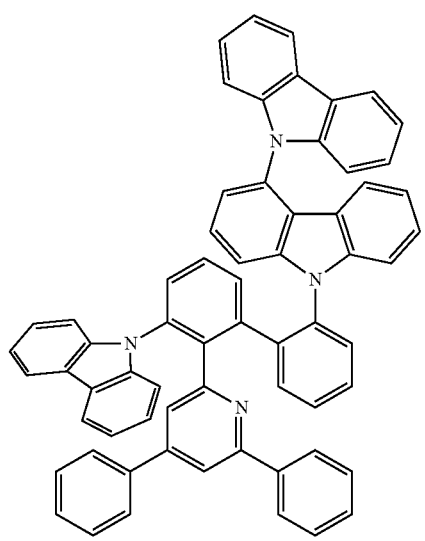
T-29

-continued
T-30
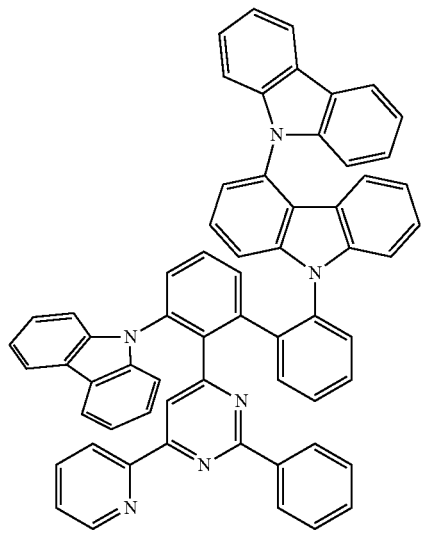
T-31
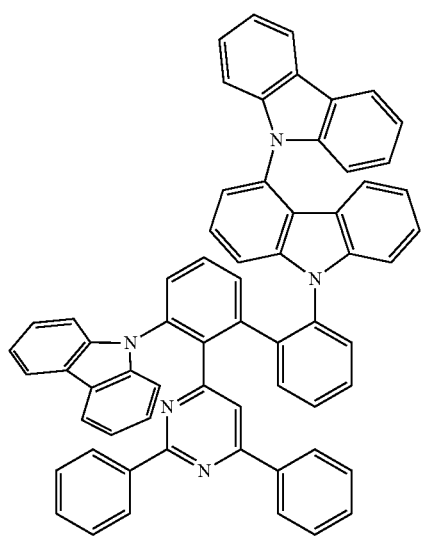
T-32
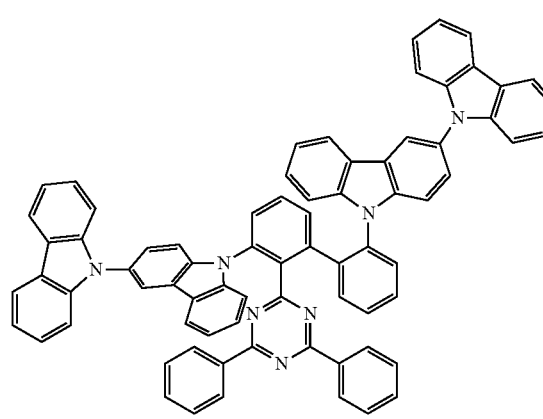
T-33
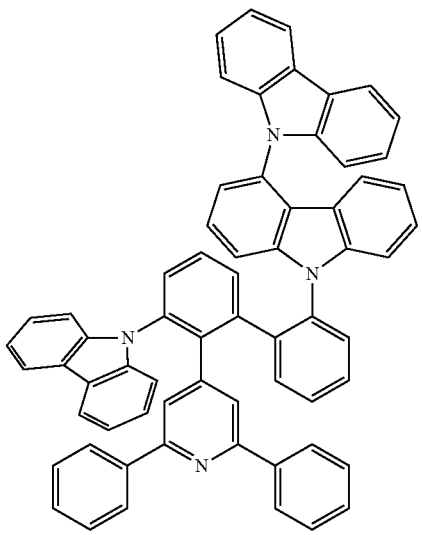
T-34
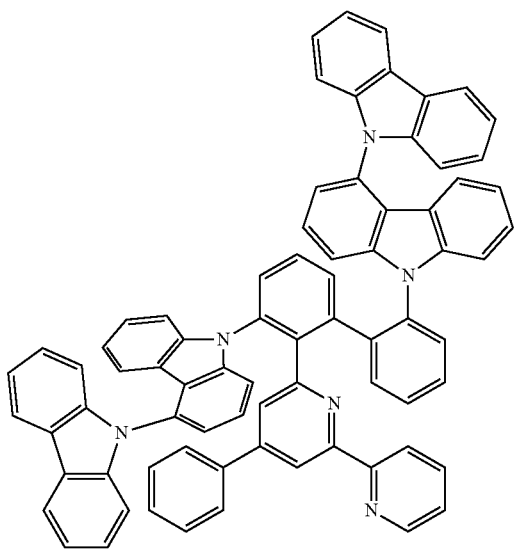
T-35
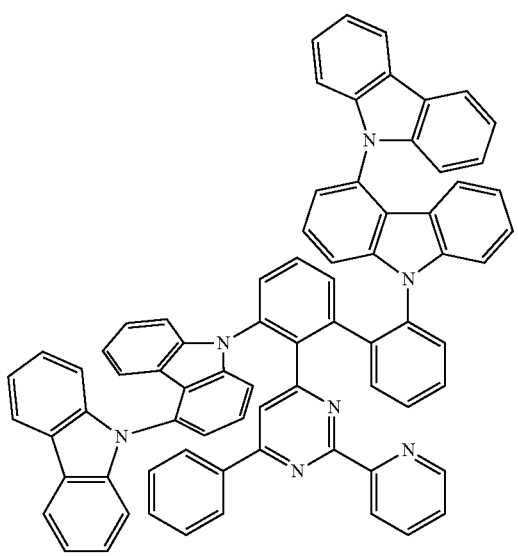

-continued
T-36
T-37
T-38
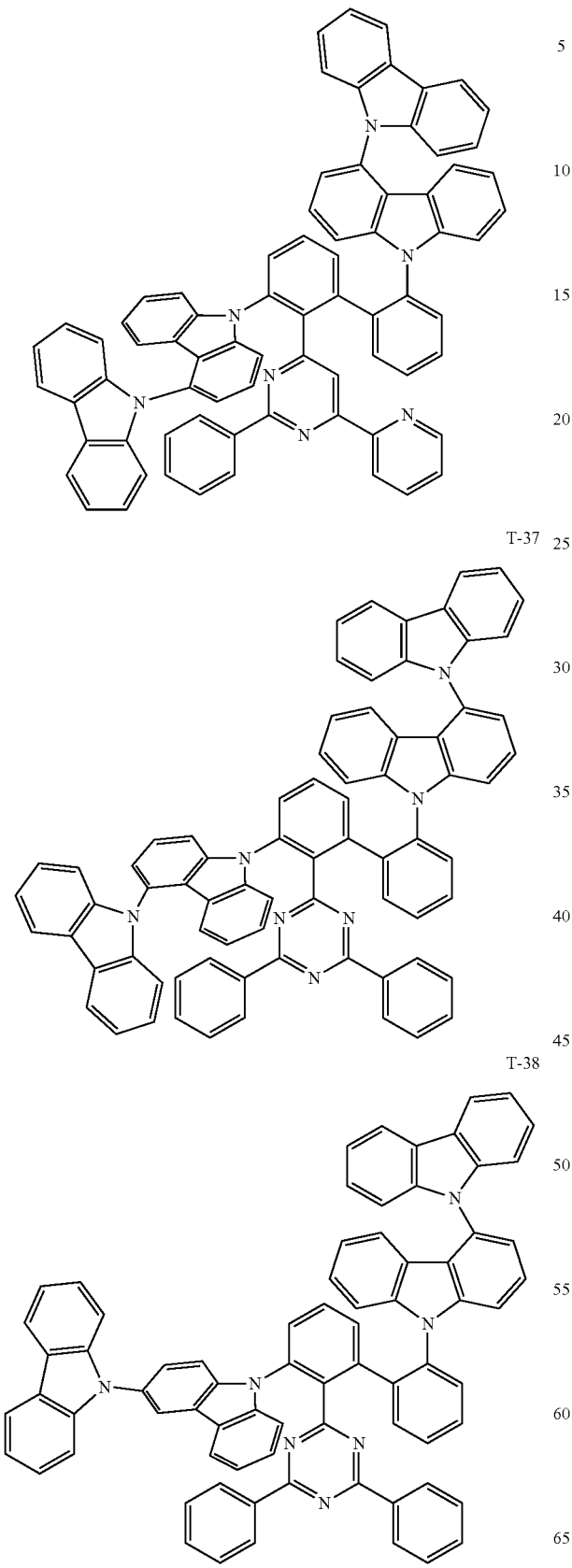
T-44
T-45

T-46
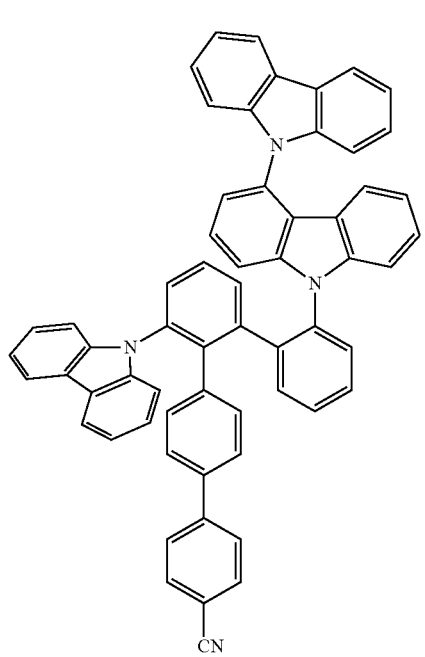
T-48
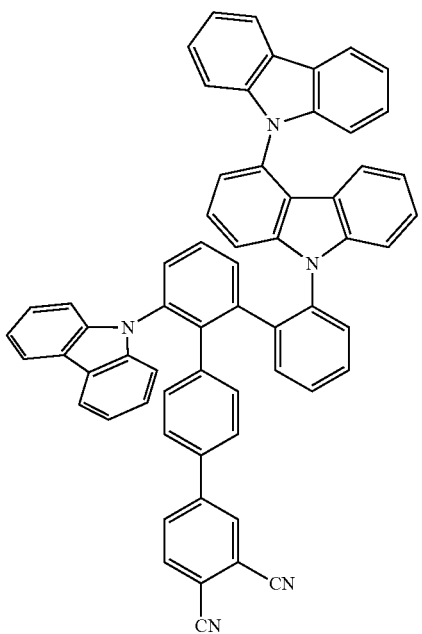
T-47
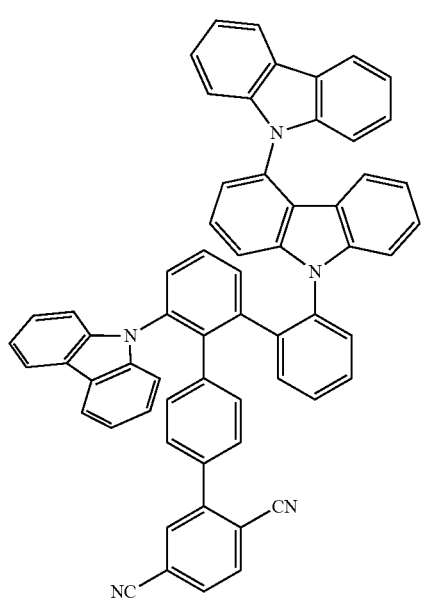
T-49
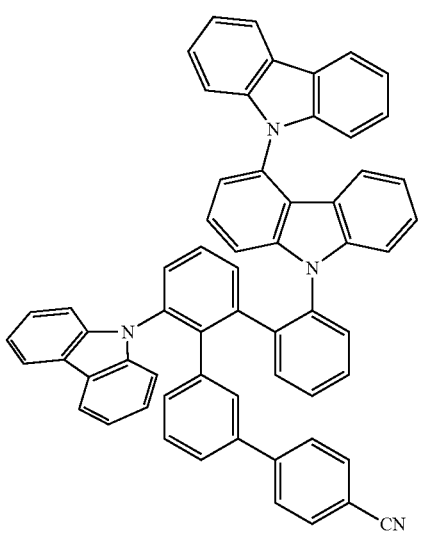

T-50
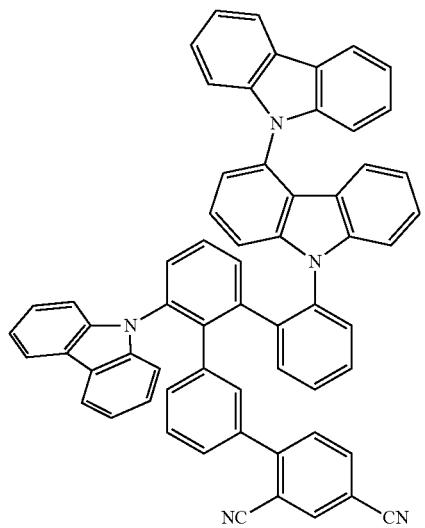
T-51
T-53
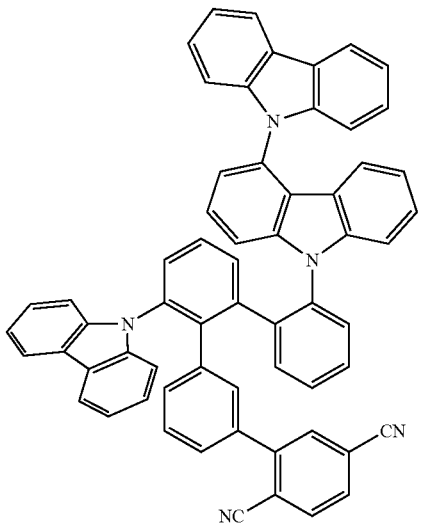
T-52
T-54
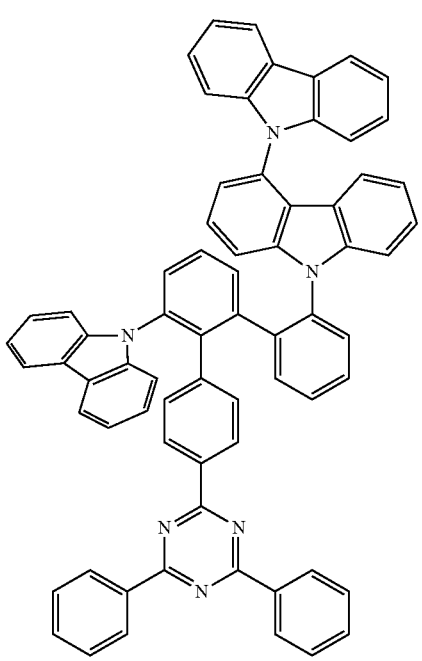

-continued

T-55

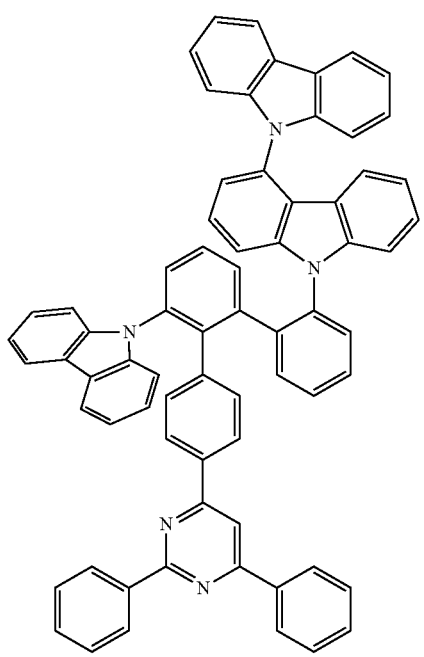

T-56

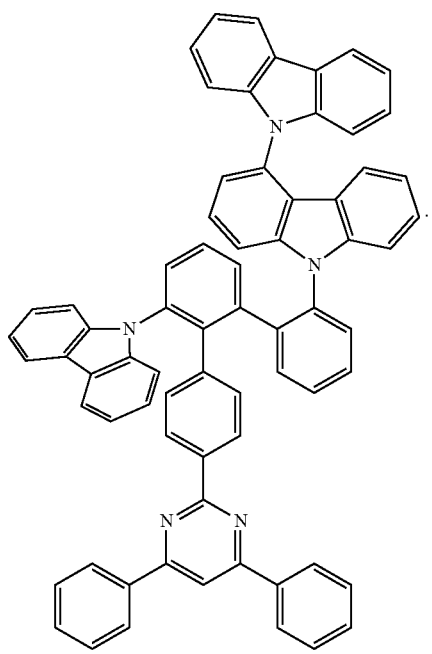

10. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a heterocyclic compound represented by Formula 1, an absolute value of a difference between a singlet energy level and a triplet energy level of the heterocyclic compound being about 0.2 eV or less:

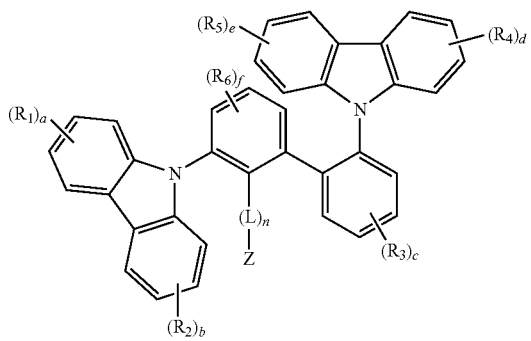

Formula 1 wherein, in Formula 1,
$R_1$ to $R_6$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
L is a substituted or unsubstituted arylene group having 6 to 30 carbon atoms for forming a ring, or a substituted or unsubstituted heteroarylene group having 2 to 30 carbon atoms for forming a ring,
a, b, c, d and e are each independently an integer of 0 to 4,
f is an integer of 0 to 3,
n is 0 or 1, and
Z is represented by Formula 2-1 or Formula 2-2:

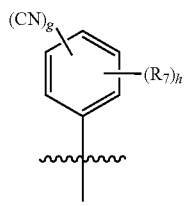

Formula 2-1

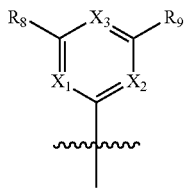

Formula 2-2 wherein, in Formula 2-1,
g is 1 or 2, when g is 1, h is an integer of 0 to 4, and when g is 2, h is an integer of 0 to 3, and
$R_7$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring,
wherein, in Formula 2-2,
$X_1$ to $X_3$ are each independently $CR_{10}$ or N,
at least one of $X_1$ to $X_3$ is N, and
$R_8$ to $R_{10}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, wherein when Z is represented by Formula 2-1, n is 1.

11. The organic electroluminescence device of claim 10, wherein the heterocyclic compound represented by Formula 1 is to emit blue light having a wavelength of less than about 470 nm.

12. The organic electroluminescence device of claim 10, wherein the heterocyclic compound represented by Formula 1 is to emit thermally activated delayed fluorescence.

13. The organic electroluminescence device of claim 10, wherein Z is represented by one of Formulae 3-1 to 3-9:

Formula 3-1

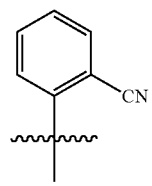

Formula 3-2

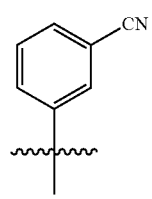

Formula 3-3

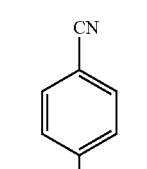

Formula 3-4

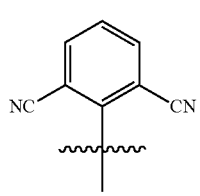

Formula 3-5

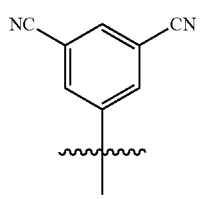

Formula 3-6

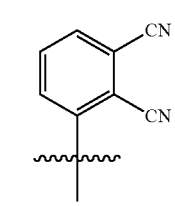

Formula 3-7

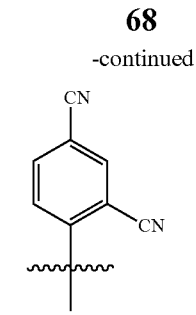

Formula 3-8

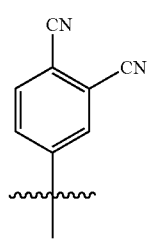

Formula 3-9

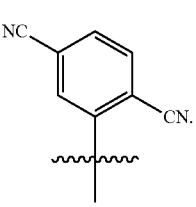

14. The organic electroluminescence device of claim 10, wherein Z is represented by Formula 2-2-1:

Formula 2-2-1

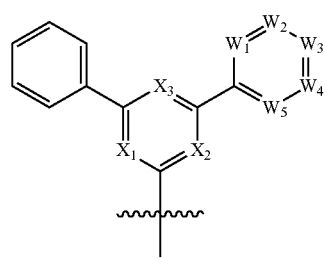

wherein, in Formula 2-2-1, $W_1$ to $W_5$ are each independently CH or N, and $X_1$ to $X_3$ are the same as defined in claim 10.

15. The organic electroluminescence device of claim 14, wherein a total number of N in $W_1$ to $W_5$ is 0 or 1.

16. The organic electroluminescence device of claim 10, wherein L is a substituted or unsubstituted phenylene group.

17. The organic electroluminescence device of claim 10, wherein at least one of $R_1$, $R_2$, $R_4$, and $R_5$ is a substituted or unsubstituted phenyl group, or a substituted or unsubstituted carbazole group.

18. The organic electroluminescence device of claim 10, wherein at least one of $R_1$, $R_2$, $R_4$, and $R_5$ is represented by one of following structures:

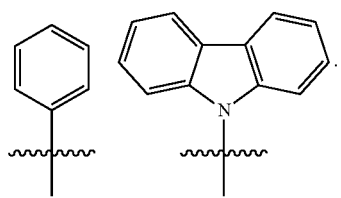
19. The organic electroluminescence device of claim 10, wherein a+b+d+e is 0, 1 or 2.
20. The organic electroluminescence device of claim 10, wherein the heterocyclic compound represented by Formula 1 is at least one selected from compounds represented in Compound Group 1:
[Compound Group 1]
T-01
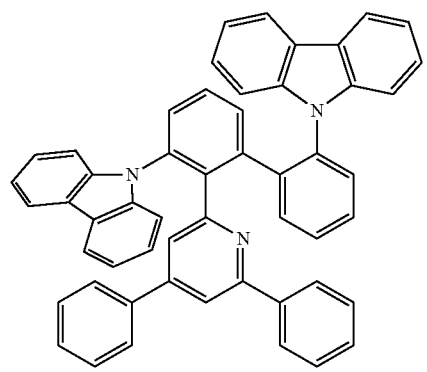
T-02
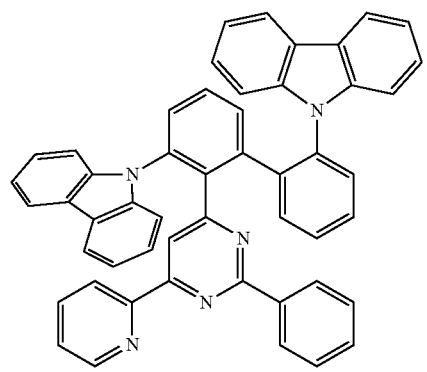
T-03
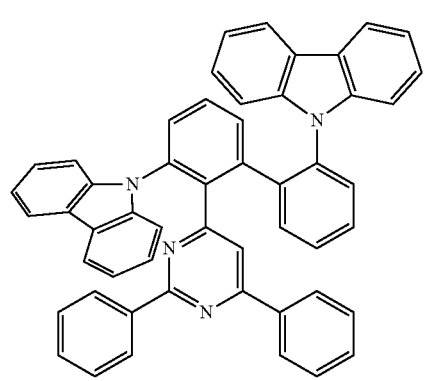
T-04
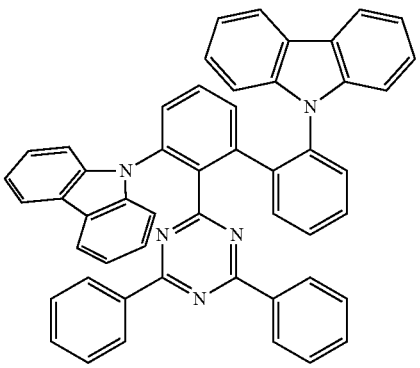
T-05
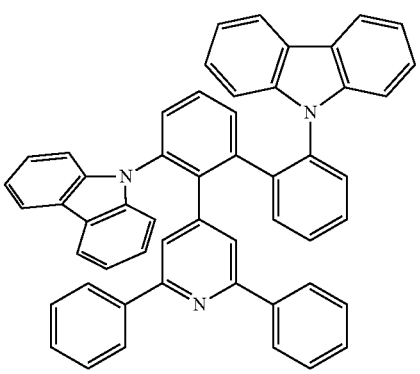
T-06
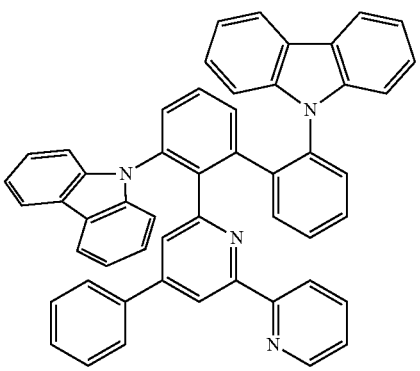
T-07
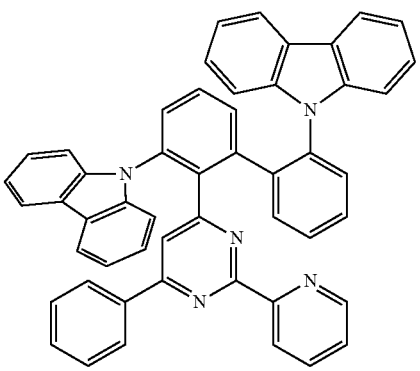

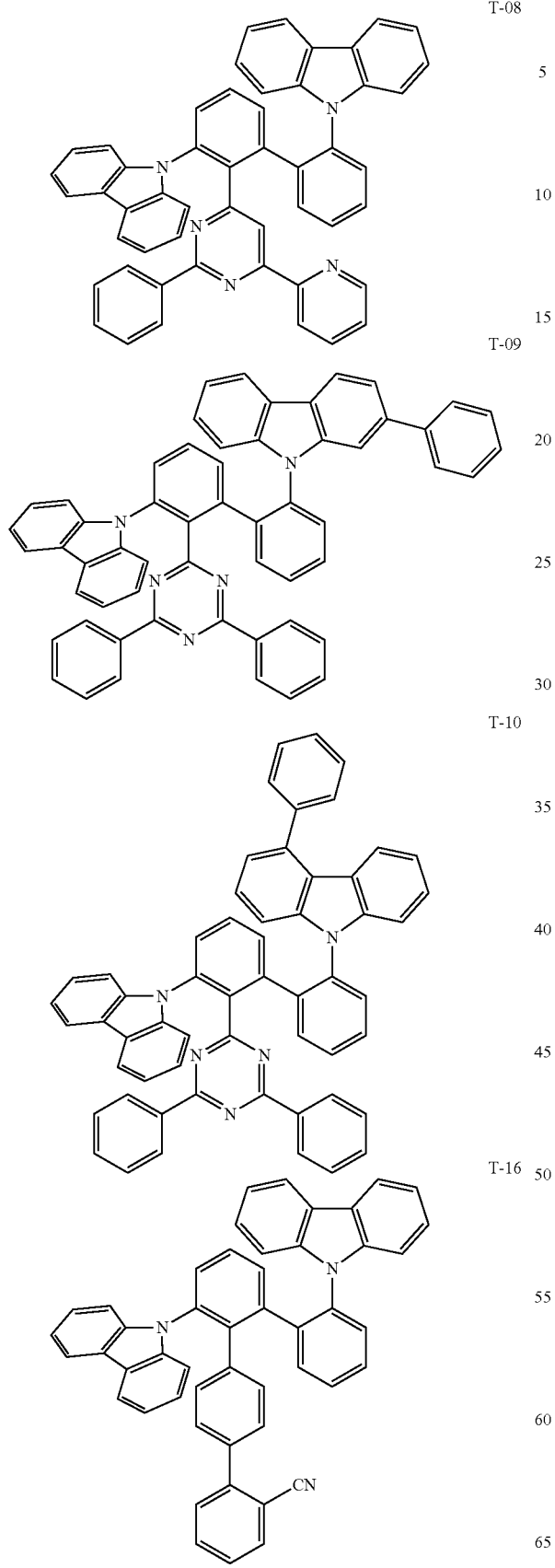
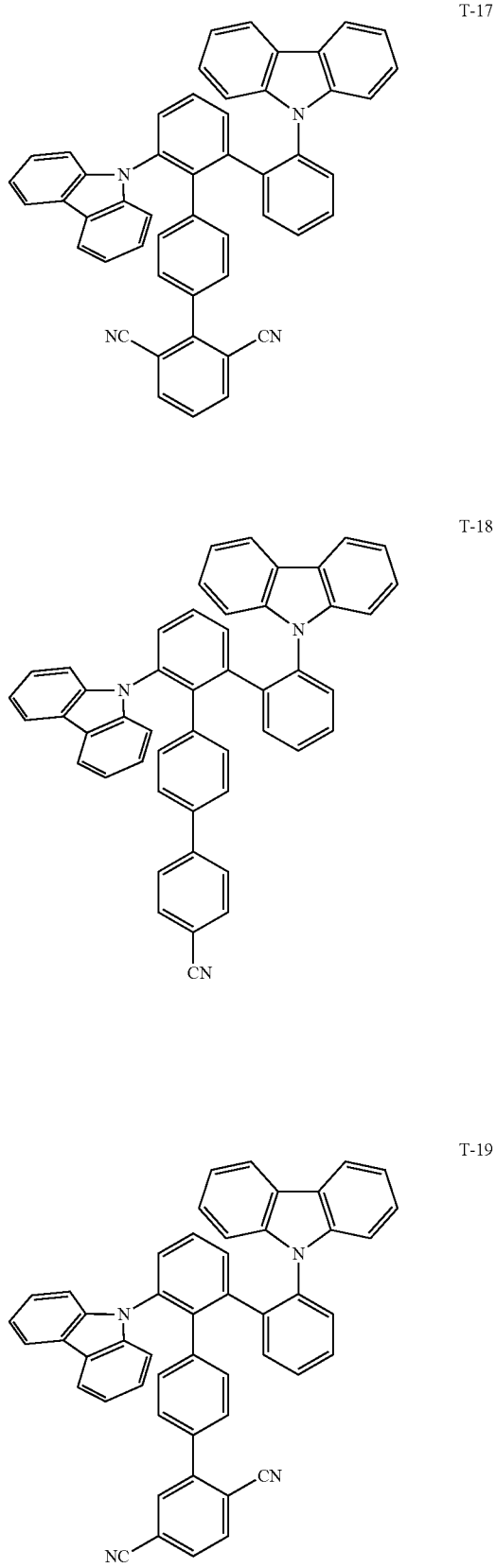

-continued
T-20
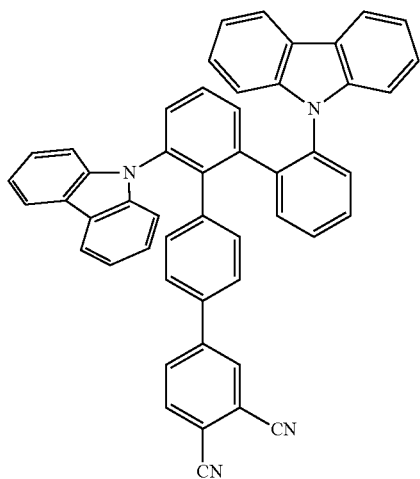
T-21
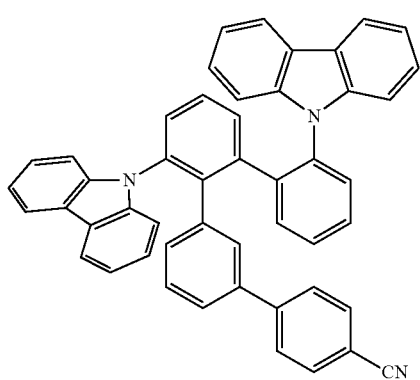
T-22
T-23
-continued
T-24
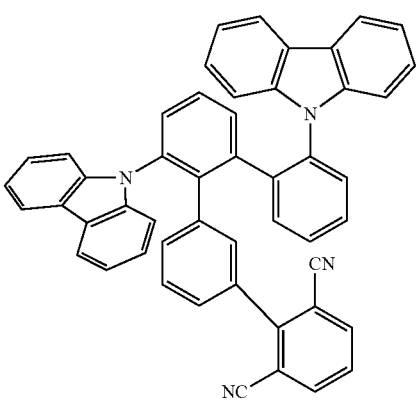
T-25
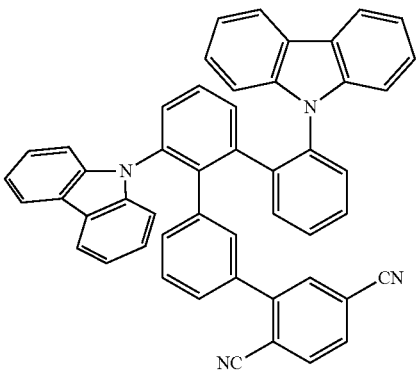
T-26
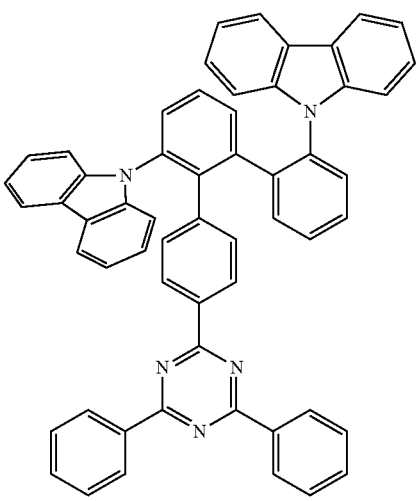

T-27
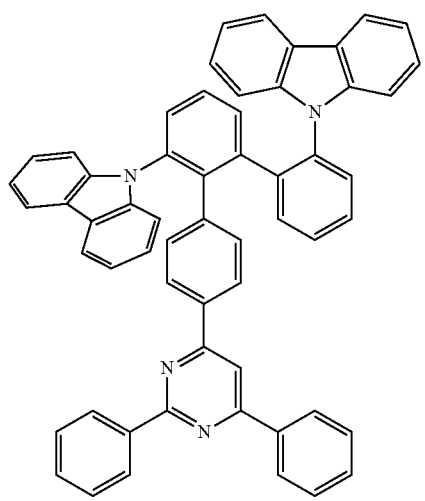
T-28
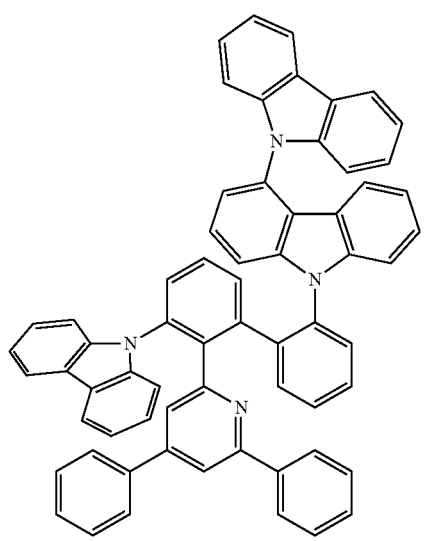
T-30
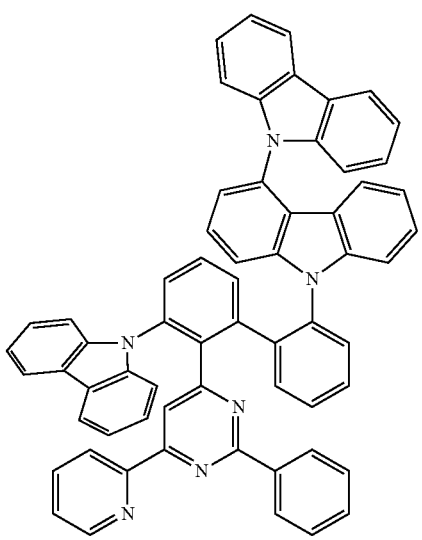
T-31
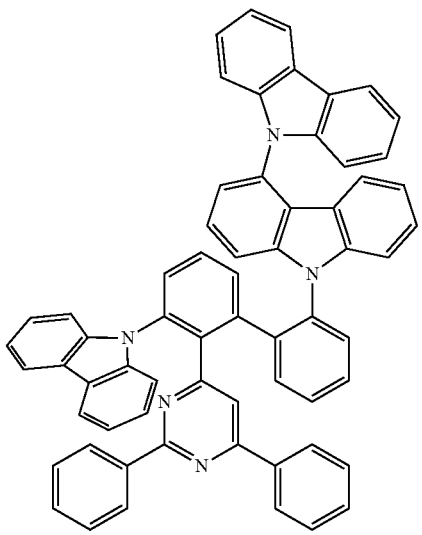
T-32
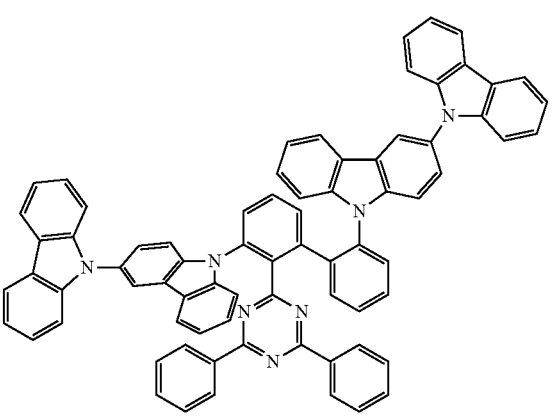

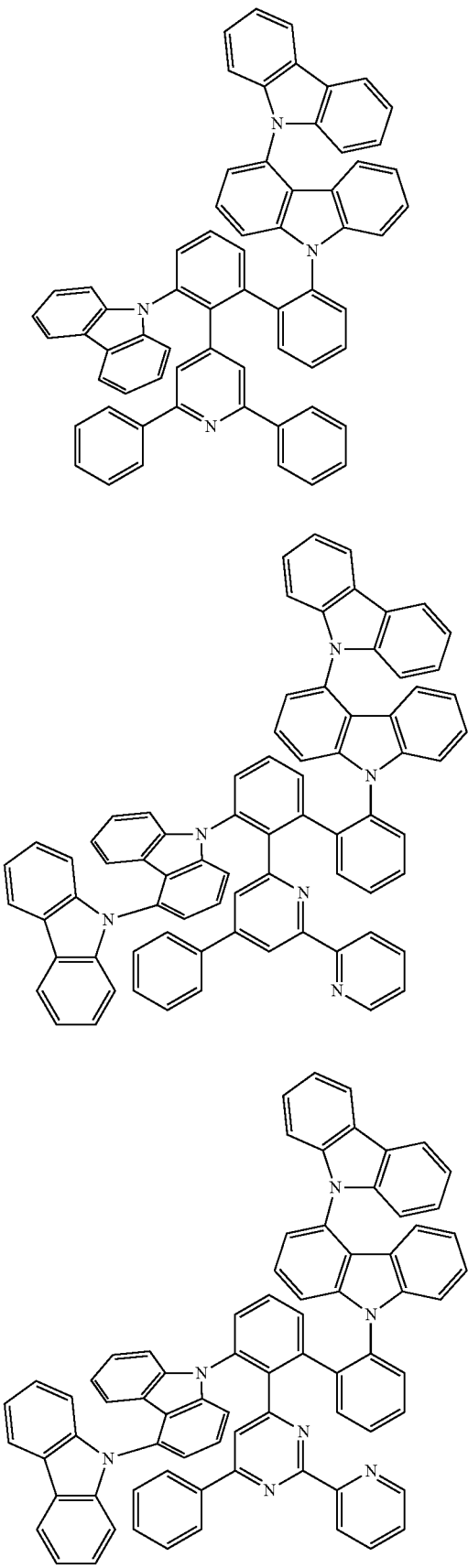

T-39
T-44
T-45
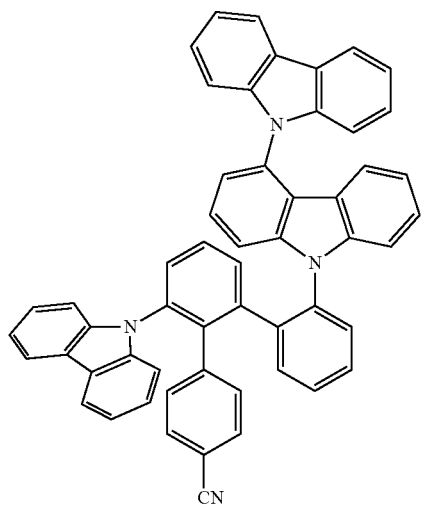
T-46
T-47
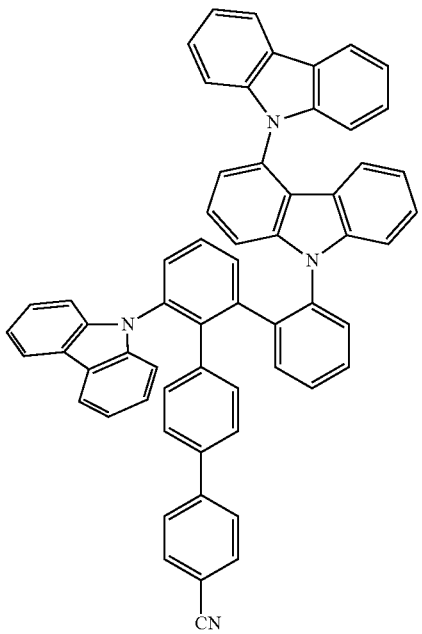
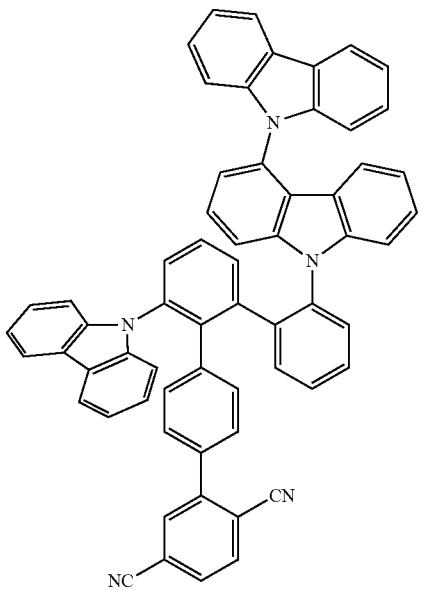

T-48
T-49
T-50
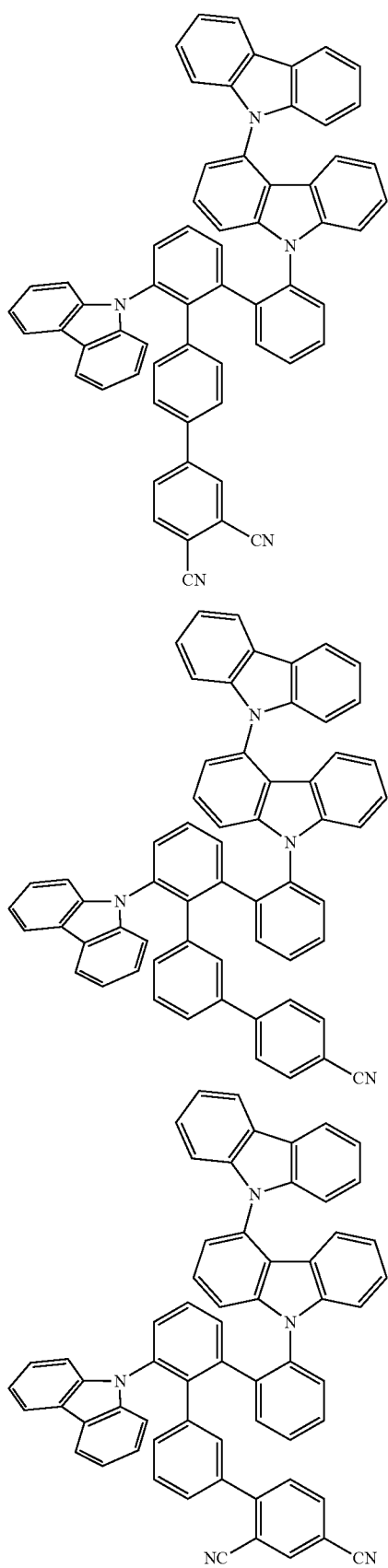
T-51
T-52

T-53
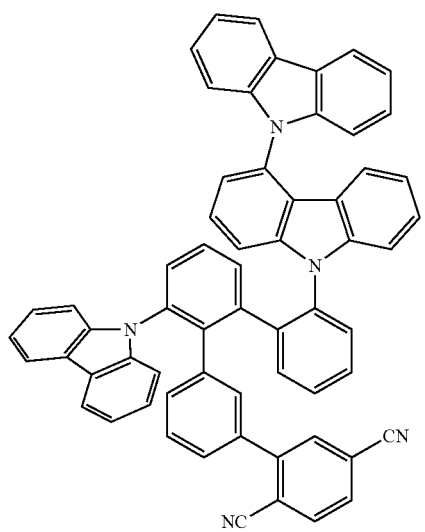
T-55
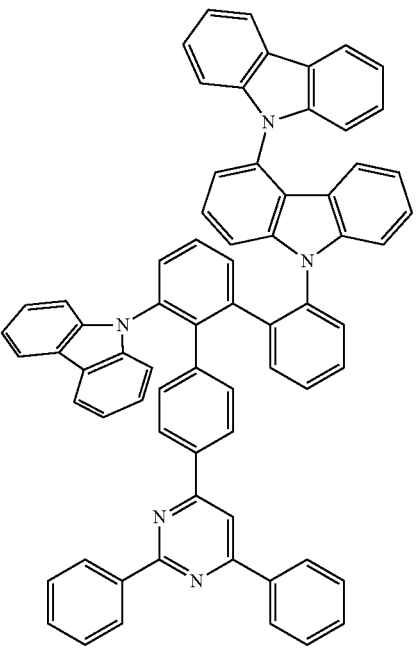
T-54
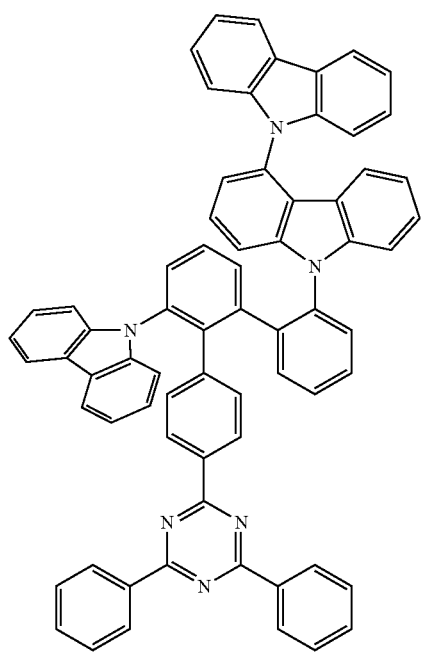
T-56
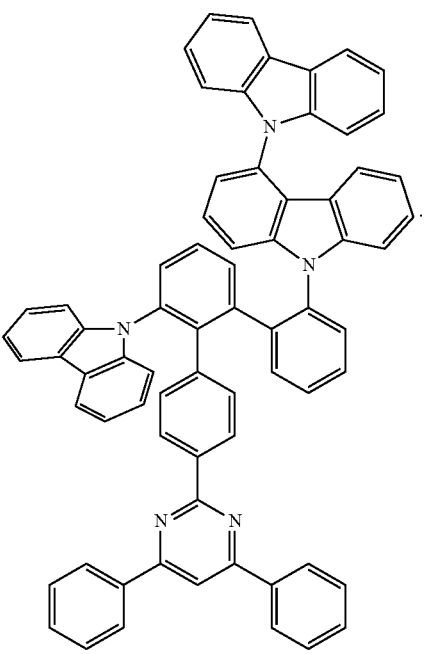
* * * * *

UNITED STATES PATENT AND TRADEMARK OFFICE
CERTIFICATE OF CORRECTION

PATENT NO. : 10,741,774 B2
APPLICATION NO. : 15/839740
DATED : August 11, 2020
INVENTOR(S) : Hiroaki Itoi Page 1 of 1

It is certified that error appears in the above-identified patent and that said Letters Patent is hereby corrected as shown below:

In the Claims

In Column 49, Line 26, Claim 3        delete "p" and insert -- g --

In Column 66, Line 55, Claim 10       delete "his" and insert -- h is --

In Column 66, Line 56, Claim 10       delete "his" and insert -- h is --

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*